(12) United States Patent
Suh et al.

(10) Patent No.: US 11,002,739 B2
(45) Date of Patent: May 11, 2021

(54) MONOCLONAL ANTIBODY SPECIFICALLY BINDING TO THIOREDOXIN 1, AND USE THEREOF

(71) Applicant: E&S HEALTHCARE CO., LTD., Daejeon (KR)

(72) Inventors: Kyong Hoon Suh, Daejeon (KR); Eun Hye Kang, Daejeon (KR); Il Han Kim, Daejeon (KR); Jong Hwan Jung, Daejeon (KR); Ki Se Lee, Sejong (KR); Mi Kyung Kim, Daejeon (KR)

(73) Assignee: E&S HEALTHCARE CO., LTD., Daejeon (KR)

( * ) Notice: Subject to any disclaimer, the term of this patent is extended or adjusted under 35 U.S.C. 154(b) by 107 days.

(21) Appl. No.: 16/332,623

(22) PCT Filed: Sep. 13, 2016

(86) PCT No.: PCT/KR2016/010381
§ 371 (c)(1),
(2) Date: Mar. 12, 2019

(87) PCT Pub. No.: WO2018/052153
PCT Pub. Date: Mar. 22, 2018

(65) Prior Publication Data
US 2020/0200750 A1 Jun. 25, 2020

(30) Foreign Application Priority Data
Sep. 13, 2016 (KR) .................. 10-2016-0118053

(51) Int. Cl.
*C07K 16/00* (2006.01)
*G01N 33/574* (2006.01)
*C07K 16/40* (2006.01)

(52) U.S. Cl.
CPC ....... *G01N 33/57415* (2013.01); *C07K 16/40* (2013.01); *C07K 2317/565* (2013.01); *G01N 2333/90* (2013.01)

(58) Field of Classification Search
CPC ......... G01N 33/57415; G01N 2333/90; C07K 16/40; C07K 2317/565
See application file for complete search history.

(56) References Cited

FOREIGN PATENT DOCUMENTS

| CN | 101493464 | 7/2009 |
|---|---|---|
| JP | H06-261783 | 9/1994 |
| KR | 2010-0104110 | 9/2010 |
| KR | 10-1058230 | 8/2011 |
| WO | WO 2005/117930 | 12/2005 |
| WO | WO 2010/107158 | 9/2010 |

OTHER PUBLICATIONS

Johnson and Wu, Methods in Molecular Biology, Antibody Engineering: Methods and Protocols, vol. 248, p. 11-25, 2004.*
Paul, Fundamental Immunology, 3rd Edition, 1993, pp. 292-295.*
Rudikoff etal, Proc. Natl. Acad. Sci. USA, 79(6): 1979-1983, Mar. 1982.*
Casset et al, Biochemical and Biophysical Research Communications, 2003, vol. 307, pp. 198-205.*
Holm et al, Molecular Immunology, 2007, vol. 44, pp. 1075-1084.*
International Search Report and Written Opinion issued in International Patent Application No. PCT/KR2016/010381, dated Jun. 7, 2017. (English Translation of Search Report).
NCBI. "immunoglobulin light chain kappa [*Mus musculus*]" GenBank accession No. CAS68984,. Feb. 28, 2003.
Park et al., "Thioredoxin 1 as a serum Marker for Breast Cancer and Its Use in Combination with CEA or CA15-3 for Improving the Sensitivity of Breast Cancer Diagnoses" *BMC Research Notes*, 2014, (7):1-12.
Tang et al., "Preparation and Identification of Monoclonal Antibodies Against Recombinant Human Thioredoxins" *Hybridoma*, 2007, 26(5):338-341.

\* cited by examiner

*Primary Examiner* — Mark Halvorson
(74) *Attorney, Agent, or Firm* — Norton Rose Fulbright US LLP

(57) ABSTRACT

The present invention relates to an antibody specifically binding to thioredoxin-1 and a use thereof, and more particularly, to an antibody specifically binding to thioredoxin-1 or an antigen-binding fragment thereof, a nucleic acid molecule(s) encoding a heavy chain and/or a light chain of the antibody or antigen-binding fragment thereof, a recombinant vector including the nucleic acid molecule, host cells, a method of preparing the antibody or antigen-binding fragment thereof, a breast cancer diagnostic kit, and a method of providing information necessary for breast cancer diagnosis.

16 Claims, 8 Drawing Sheets
Specification includes a Sequence Listing.

(a)
SEQUENCE: >Unnamed-1

```
  1  QIVLTQSPAIMSASPGEKVTMTCSASSRLSYMYWYQQKPGTSPKRWIYDTSKLASGVPARFSGSGSGTSYSLTISTMEAE
 81  DAATYYCHQRSSYPTFGAGTKLEIKRADAAPTVSIFPPSSEQLTSGGASVVCFLNNFYPKDINVKWKIDGSERQNGVLNS
161  WTDQDSKDSTYSMSSTLTLTKDEYERHNSYTCEATHKTSTSPIVKSFNRNEC (SEQ ID NO: 25)
```

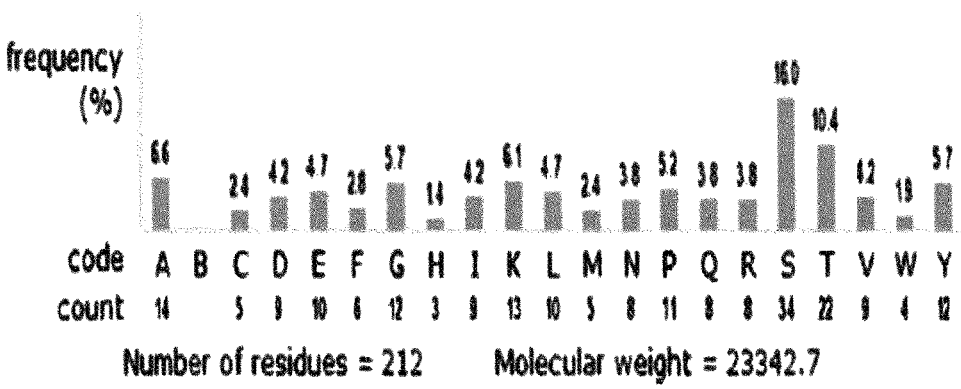

Number of residues = 212    Molecular weight = 23342.7

(b)
SEQUENCE: >Unnamed-1

```
  1  EVQLQQSGAELVKPGASVKLSCTASGFNIKDTFMHWVKQRPEQGLEWIGRIDPANGNTKYDPKFQGKATITADTSSNTAY
 81  LQLSSLTSEDTAVYYCALLQYSAMDYWGQGTSVTVSSAKTTPPSVYPLAPGCGDTTGSSVTLGCLVKGYFPESVTVTWNS
161  GSLSSSVHTFPALLQSGLYTMSSSVTVPSSTWPSQTVTCSVAHPASSTTVDKKLEPSGPISTINPCPPCKECHKCPAPNL
241  EGGPSVFIFPPNIKDVLMISLTPKVTCVVVDVSEDDPDVQISWFVNNVEVHTAQTQTHREDYNSTIRVVSTLPIQHQDWM
321  SGKEFKCKVNNKDLPSFIERTISKIKGLVRAPQVYILPPPAEQLSRKDVSLTCLVVGFNPGDISVEWTSNGHTEENYKDT
401  APVLDSDGSYFIYSKLNMKTSKWEKTDSFSCNVRHEGLKNYYLKKTISRSPG (SEQ ID NO: 26)
```

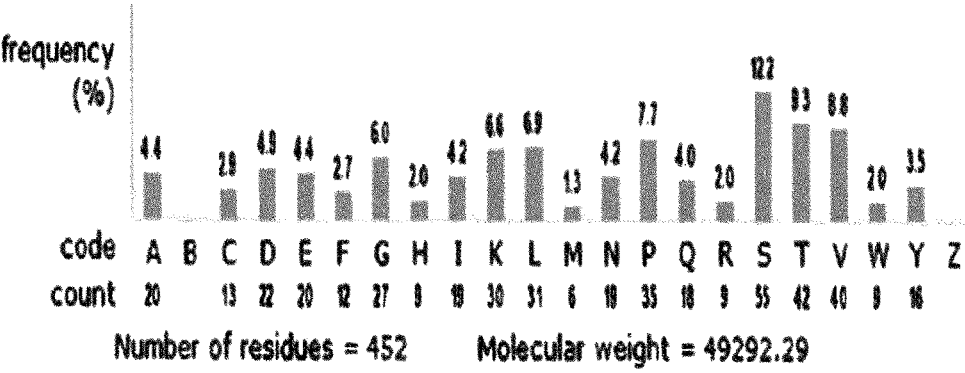

Number of residues = 452    Molecular weight = 49292.29

SEQUENCE: >Unnamed-1

```
1   DVLMTQTPLSLPVSLGDQASISCRSSQSIVHSNGNTYLEWYLQKPGQSPKLLLYKVSNRFSGVPDRFSGSGSGTDFTLKI
81  SRVEAEDLGVYYCFQGSHVPYTPGGGTKLEIKRADAAPTVSIFPPSSEQLTSGGASVVCFLNNFYPKDINVKWKIDGSER
161 QNGVLNSWTDQDSKDSTYSMSSTLTLTKDEYERHNSYTCEATHKTSTSPIVKSFNRNEC  (SEQ ID NO: 27)
```

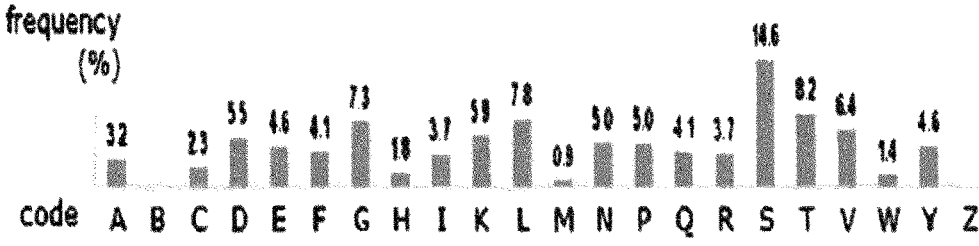

Number of residues = 219   Molecular weight = 24157.65

(b)

SEQUENCE: >Unnamed-1

```
1   QVQLQQSGAELARPGASVKMSCKASGYTFTSYTMHWVKQRPGQGLEWIGYINPTSDYTNYNQRFKDKATLTADKSSSTAY
81  MQLSSLTSEDSAVYFCASEGGPLYYFDYWGQGTTLTVSSAKTTPPSVYPLAPGSAAQTNSMVTLGCLVKGYFPEPVTVTW
161 NSGSLSSGVHTFPAVLQSDLYTLSSSVTVPSSTWPSETVTCNVAHPASSTKVDKKIVPRDCGCKPCICTVPEVSSVFIFP
241 PKPKDVLTITLTPKVTCVVVDISKDDPEVQFSWFVDDVEVHTAQTQPREEQFNSTFRSVSELPIMHQDWLNGKEFKCRVN
321 SAAFPAPIEKTISKTKGRPKAPQVYTIPPPKEQMAKDKVSLTCMITDFFPEDITVEWQWNGQPAENYKNTQPIMDTDGSY
401 FVYSKLNVQKSNWEAGNTFTCSVLHEGLHNHHTEKSLSHSPG  (SEQ ID NO: 28)
```

Number of residues = 442   Molecular weight = 48807.7

FIG. 3

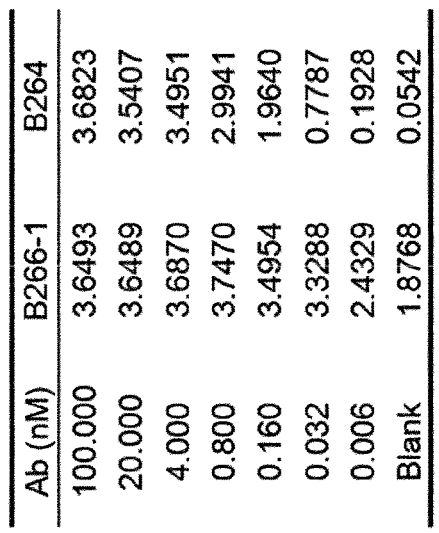
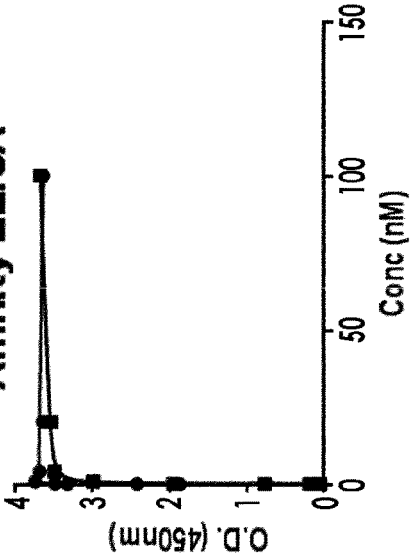
FIG. 8

MONOCLONAL ANTIBODY SPECIFICALLY BINDING TO THIOREDOXIN 1, AND USE THEREOF

CROSS-REFERENCE TO RELATED APPLICATIONS

This application is a national phase application under 35 U.S.C. § 371 of International Application No. PCT/KR2016/010381, filed on Sep. 13, 2016, which claims priority to and the benefit of Korean Patent Application No. 10-2016-0118053, filed on Sep. 13, 2016, the disclosures of which are incorporated herein by reference in their entirety.

SEQUENCE LISTING

The instant application contains a Sequence Listing which has been filed electronically in ASCII format and is hereby incorporated by reference in its entirety. Said ASCII copy, created on Feb. 3, 2021, is named SequenceListing.txt and is 35,791 bytes in size.

FIELD OF THE DISCLOSURE

The present invention relates to a monoclonal antibody specifically binding to thioredoxin-1 and a use thereof, and more particularly, to a monoclonal antibody specifically binding to thioredoxin-1 or an antigen-binding fragment thereof, a nucleic acid molecule encoding a heavy chain and/or a light chain of the antibody or antigen-binding fragment thereof, a recombinant vector including the nucleic acid molecule, host cells, a method of preparing the antibody or antigen-binding fragment thereof, a breast cancer diagnostic kit, and a method of providing information necessary for breast cancer diagnosis.

DESCRIPTION OF RELATED ART

Thioredoxin (Trx) is a small redox protein of about 12 kDa, which is present in the reduced state by a thioredoxin reductase through NADPH-dependent reduction, and includes thioredoxin-1 (Trx1) and thioredoxin-2 (Trx2) in mammals. Thioredoxin acts as a growth factor, removes hydrogen peroxide which is toxic in cells, promotes binding of critical factors relating to the role of a ribonucleotide reductase and transcription in bacteria to DNA, and affects the activity of a transcription factor such as nuclear transcription factor kB (NF-kB) in eukaryotic cells. Therefore, thioredoxin affects cell death and tumors and thus plays a pivotal role in regulation of cancer cell growth, and cleaves a disulfide bond of another oxidized protein to assist the maintenance of activity in a reduced state. Thioredoxin-1 and 2 reductases remove nitrogen oxide of cysteines in mammalian cells to affect cell death, and have potential significance in various diseases including an inflammatory disease, a heart attack, and cancer. In addition, immunohistochemical analysis using an anti-thioredoxin antibody shows the expression of thioredoxin in human cancer tissues including the liver, colon, pancreas and cervix, and such expression indicates the possibility of involving thioredoxin in tumorigenesis.

Under these circumstances, the inventors had studied a marker for breast cancer diagnosis which can diagnose breast cancer or predict a prognosis thereof early, thioredoxin-1 was lowly expressed in normal breast tissue, but very highly expressed in breast cancer tissue, demonstrating that thioredoxin-1 is useful as a marker for breast cancer diagnosis (Korean Patent No. 10-1058230).

To develop in vitro diagnostics (IVD) based on an enzyme-linked immunosorbent assay (ELISA) to have high accuracy and high precision, a pair of antibodies having different sites with different affinities to the same antigen protein are required. Moreover, it is necessary to have a system producing antibodies having a certain affinity every time with low costs. In the present invention, to detect thioredoxin-1 (Trx1) present in human serum, two types of high-performance recombinant monoclonal antibodies were developed, the antibodies very specifically bind to thioredoxin-1 and thus can be useful for screening breast cancer patients. Therefore, the present invention was completed.

SUMMARY OF THE INVENTION

The present invention is directed to providing a monoclonal antibody capable of diagnosing breast cancer with high sensitivity and high specificity or an antigen-binding fragment thereof.

The present invention is also directed to providing a nucleic acid molecule encoding a heavy chain and/or light chain of the monoclonal antibody or antigen-binding fragment thereof.

The present invention is also directed to providing a recombinant vector including the nucleic acid molecule.

The present invention is also directed to providing host cells including the recombinant vector.

The present invention is also directed to providing a method of preparing a monoclonal antibody specifically binding to thioredoxin-1 or an antigen-binding fragment thereof, which includes culturing the host cells.

The present invention is also directed to providing a breast cancer diagnostic kit, which includes the above-described monoclonal antibody or antigen-binding fragment thereof.

The present invention is directed to providing a method of providing information necessary for breast cancer diagnosis using the above-described monoclonal antibody or antigen-binding fragment thereof.

To solve the above-described problems, the present invention provides a monoclonal antibody specifically binding to thioredoxin-1 or an antigen-binding fragment thereof, which includes a light chain variable region, which includes a light chain CDR1 consisting of the amino acid sequence of SEQ ID NO: 4, a light chain CDR2 consisting of the amino acid sequence of SEQ ID NO: 5 and a light chain CDR3 consisting of the amino acid sequence of SEQ ID NO: 6; and a heavy chain variable region.

According to an exemplary embodiment of the present invention, the antibody may include a light chain variable region consisting of the amino acid sequence of SEQ ID NO: 11 and a heavy chain variable region.

According to another exemplary embodiment of the present invention, the antibody may include a light chain consisting of the amino acid sequence of SEQ ID NO: 15 and a heavy chain consisting of the amino acid sequence of SEQ ID NO: 16.

The present invention also provides a monoclonal antibody specifically binding to thioredoxin-1 or an antigen-binding fragment thereof, which includes a light chain variable region which includes a light chain CDR1 consisting of the amino acid sequence of SEQ ID NO: 1, a light chain CDR2 consisting of the amino acid sequence of SEQ ID NO: 2 and a light chain CDR3 consisting of the amino acid sequence of SEQ ID NO: 3; and a heavy chain variable region, which includes a heavy chain CDR1 consisting of the amino acid sequence of SEQ ID NO: 7, a heavy chain CDR2 consisting of the amino acid sequence of SEQ ID NO: 8 and a heavy chain CDR3 consisting of the amino acid sequence of SEQ ID NO: 9.

According to an exemplary embodiment of the present invention, the antibody may include a light chain variable region consisting of the amino acid sequence of SEQ ID NO: 10 and a heavy chain variable region consisting of the amino acid sequence of SEQ ID NO: 12.

According to another exemplary embodiment of the present invention, the antibody may include a light chain consisting of the amino acid sequence of SEQ ID NO: 13 and a heavy chain consisting of the amino acid sequence of SEQ ID NO: 14.

According to still another exemplary embodiment of the present invention, the antibody may include an IgG1 heavy chain and a kappa (κ) light chain.

According to yet another exemplary embodiment of the present invention, the antigen-binding fragment may be a Fab, F (ab'), F (ab')$_2$, Fv or a single-chain antibody molecule.

According to yet another exemplary embodiment of the present invention, the antibody may be a chimeric antibody, a humanized antibody, or a human antibody.

The present invention provides a nucleic acid molecule encoding a heavy chain and/or a light chain of the above-described antibody or antigen-binding fragment thereof.

According to an exemplary embodiment of the present invention, the nucleic acid molecule encoding a light chain may be the nucleotide sequence of SEQ ID NO: 17 or the nucleotide sequence of SEQ ID NO: 19.

According to an exemplary embodiment of the present invention, the nucleic acid molecule encoding a heavy chain may be the nucleotide sequence of SEQ ID NO: 18 or the nucleotide sequence of SEQ ID NO: 20.

The present invention also provides a recombinant vector including the nucleic acid molecule encoding a heavy chain, the nucleic acid molecule encoding a light chain, or the nucleic acid molecules encoding both of a heavy chain and a light chain.

The present invention provides host cells including the recombinant vector and a method of preparing a monoclonal antibody specifically binding to thioredoxin-1 or an antigen-binding fragment thereof, which includes culturing the host cells.

The present invention also provides a breast cancer diagnostic kit, which includes the above-described antibody or antigen-binding fragment thereof.

According to an exemplary embodiment of the present invention, the kit may be an enzyme linked immunosorbent assay (ELISA) kit.

According to another exemplary embodiment of the present invention, the ELISA may be any one selected from the group consisting of direct ELISA, indirect ELISA, direct sandwich ELISA and indirect sandwich ELISA.

The present invention also provides a method of providing information necessary for breast cancer diagnosis, which includes: (a) bringing the monoclonal antibody or antigen-binding fragment thereof of any one of claims 1 to 4 into contact with a biological sample isolated from a subject suspected of having breast cancer; (b) measuring an expression level of the thioredoxin-1 protein binding to the monoclonal antibody or an antigen-binding fragment thereof in the biological sample through the formation of an antigen-antibody complex; and (c) comparing the expression level of the thioredoxin-1 protein, measured in step (b) with that of a control and, if the protein expression level is higher than that of the control, determining the subject to be a breast cancer patient.

Further, the present invention provides a method of providing information necessary for breast cancer diagnosis, which includes: (a) coating a solid support with the monoclonal antibody or an antigen-binding fragment thereof of claim 2, 4 or 6; (b) applying a biological sample isolated from a subject suspected of having breast cancer to the coated solid support; (c) removing an unbound sample; (d) applying the monoclonal antibody or an antigen-binding fragment thereof of claim 1, 3 or 5 to the solid support; (e) removing an unbound monoclonal antibody or an antigen-binding fragment thereof; (f) measuring an expression level of the thioredoxin-1 protein; and (g) comparing the expression level of the thioredoxin-1 protein, measured in step (f), with that of a control, and, if the protein expression level is higher than that of the control, determining the subject to be a breast cancer patient.

According to an exemplary embodiment of the present invention, the expression level of the thioredoxin-1 protein may be measured by any one method selected from the group consisting of western blotting, ELISA, sandwich ELISA, a radioimmunoassay, radioimmunoprecipitation, Ouchterlony immunodiffusion, an immunoprecipitation assay, a complement fixation assay, an immunochromatographic assay, FACS and a protein chip assay.

According to another exemplary embodiment of the present invention, the isolated biological sample may be any one or more selected from the group consisting of whole blood, serum, plasma, breast tissue and breast cells.

Unless defined otherwise, all technical and scientific terms used in the specification have the same meaning as commonly understood by one of ordinary skill in the art to which the invention belongs. Generally, the nomenclature used herein is well known and commonly used in the art.

The definitions of key terms used herein are as follows.

The term "antigen" refers to a molecule which can be bound by an antibody, and can be used in an animal to produce an antibody capable of binding to an epitope of the antigen or a part of the molecule. The antigen may have one or more epitopes.

The term "antibody" or "Ab" is an immunoglobulin molecule which can recognize a specific target or antigen, for example, a carbohydrate, a polynucleotide, a lipid or a polypeptide through one or more antigen recognition sites, located in a variable region of the immunoglobulin molecule, and bind thereto. The term "antibody" used herein may refer to any type of antibody, which encompasses, but is not limited to, a monoclonal antibody; a polyclonal antibody; an "antigen-binding fragment" of an antibody possessing an ability of specifically binding to a specific antigen (e.g., Trx1), for example, Fab, Fab', F(ab')$_2$, Fd, Fv, Fc, etc.; an isolated complementarity-determining region (CDR); a bispecific antibody; a hetero-conjugated antibody, or a mutant thereof; an antibody, or a fusion protein having an antigen-binding fragment (e.g., a domain antibody); a single-chain variable fragment (ScFv) and a single domain antibody [e.g., shark and camelid antibodies]; a maxibody, a minibody, an intrabody, a diabody, a triabody, a tetrabody, v-NAR and bis-scFv; a humanized antibody; a chimeric antibody; and all other modified configurations of an immunoglobulin molecule including an antigen recognition site with required specificity (including glycosylated variants of an antibody, amino acid sequence variants of an antibody and a covalently modified antibody). The antibody may be derived from a mouse, a rat, a human, or any other origin (including a chimeric or humanized antibody).

An antibody or polypeptide which "specifically binds" to a specific target or antigen (e.g., Trx1 protein) is a term generally understood in the related art, and a method of determining such specific binding has also been widely known in the related art. A specific molecule is considered to have "specific binding" when reacting or linked to a special cell or material more frequently, more rapidly, more consistently and/or with higher affinity than that with another type of cells or material. A specific antibody "specifically binds" to a specific target or antigen with higher affinity, higher binding activity, more rapidly and/or more consistently than when binding to another material.

The term "binding affinity" or "$K_D$" used herein refers to an equilibrium dissociation constant of a particular antigen-antibody interaction. $K_D$ is a ratio of a dissociation rate (also referred to as "release rate" or "$k_d$") to a binding rate or an "operation rate" or "$k_a$ (association rate constant)". Therefore, $K_D$ is $k_d/k_a$, which is expressed as molar concentration (M). It concludes that the lower $K_D$, the higher binding affinity. Therefore, a $K_D$ of 1 μM indicates a lower binding affinity, compared with a $K_D$ of 1 nM. The $K_D$ value of the antibody may be determined using a method widely established in the art. One method of determining the $K_D$ of an antibody typically utilizes surface plasmon resonance using a biosensor system, for example, a Biacore® system.

The term "vector" includes a nucleic acid molecule capable of delivering a linked different nucleic acid. One type of vector is a "plasmid," and refers to a circular double-stranded DNA loop into which an additional DNA fragment can be ligated. A different type of vector is a viral vector, and here, an additional DNA fragment may be attached to a viral genome. Some vectors can be self-replicated in host cells into which they are introduced (e.g., a bacterial vector having a bacterial origin of replication and an episomal mammalian vector). Other vectors (e.g., a non-episomal mammalian vector) may be integrated into the genome of host cells when introduced into the host cells, and thus replicated in accordance with the host genome. In addition, some vectors may direct the expression of operatively linked genes. The vectors are referred to as "recombinant expression vectors" (or simply as "expression vectors") in the specification. Generally, the expression vector useful in the recombinant DNA technique is often present in the form of a plasmid. The "plasmid" and "vector" used herein are the types of vectors most generally used, and thus can be interchangeably used. However, the present invention is to include different types of expression vectors having the same function, for example, viral vectors (e.g., a replication-deficient retrovirus, an adenovirus, and an adeno-related virus).

The term "host cells" is used to express cells which are transformed, or transformed by a nucleic acid sequence to express a selected gene of interest. The term encompasses the descendants of mother cells whether or not the descendants are identical to the original parent in the morphological or genetic aspect, as long as the selected gene is present.

A monoclonal antibody of the present invention has excellent binding affinity to thioredoxin-1, thereby very specifically binding to thioredoxin-1, and has very high sensitivity and specificity, thereby being effectively used in screening a breast cancer patient. Further, detection of thioredoxin-1 using the monoclonal antibody specifically binding to thioredoxin-1 of the present invention, rather than detection using a conventional breast cancer diagnostic biomarker CA15-3, exhibits exceptionally high sensitivity and specificity, and thus the accuracy and reliability of breast cancer diagnosis can be significantly increased.

BRIEF DESCRIPTION OF THE DRAWINGS

FIG. 2 shows the amino acid sequences of a light chain (a) and a heavy chain (b) of a 9G7(AB1) antibody obtained in Example 1.

FIG. 3 shows the amino acid sequences of a light chain (a) and a heavy chain (b) of a 2B4(AB2) antibody obtained in Example 1.

FIG. 8 shows results of analyzing the affinity of the antibody B266-1 and the antibody B264, where (a) shows a reaction value according to an antibody concentration and a graph thereof, and (b) shows the result of analyzing the affinity of antibodies using a Prism program.

DETAILED DESCRIPTION OF THE INVENTION

Figure 1:
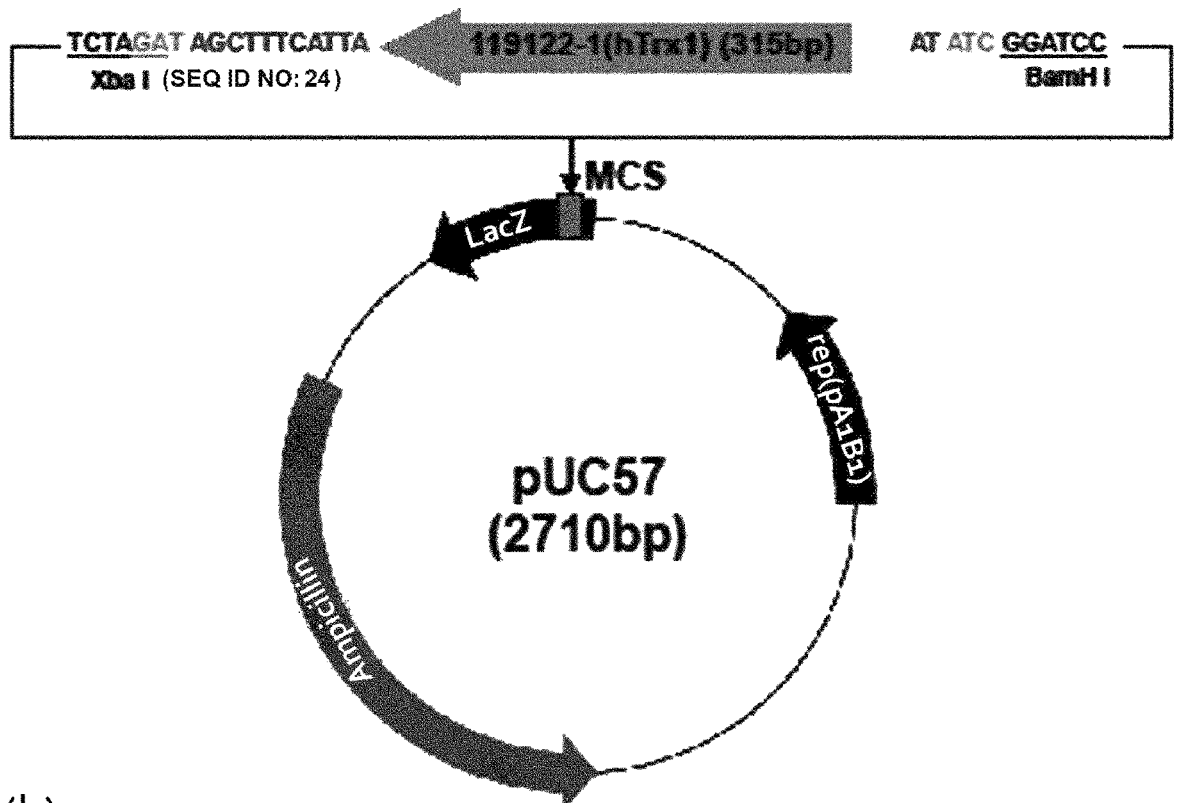
FIG. 1 shows the cleavage map of a recombinant vector expressing the thioredoxin-1 antigen and an isotyping result of an antibody obtained in Example 1.
Figure 4:
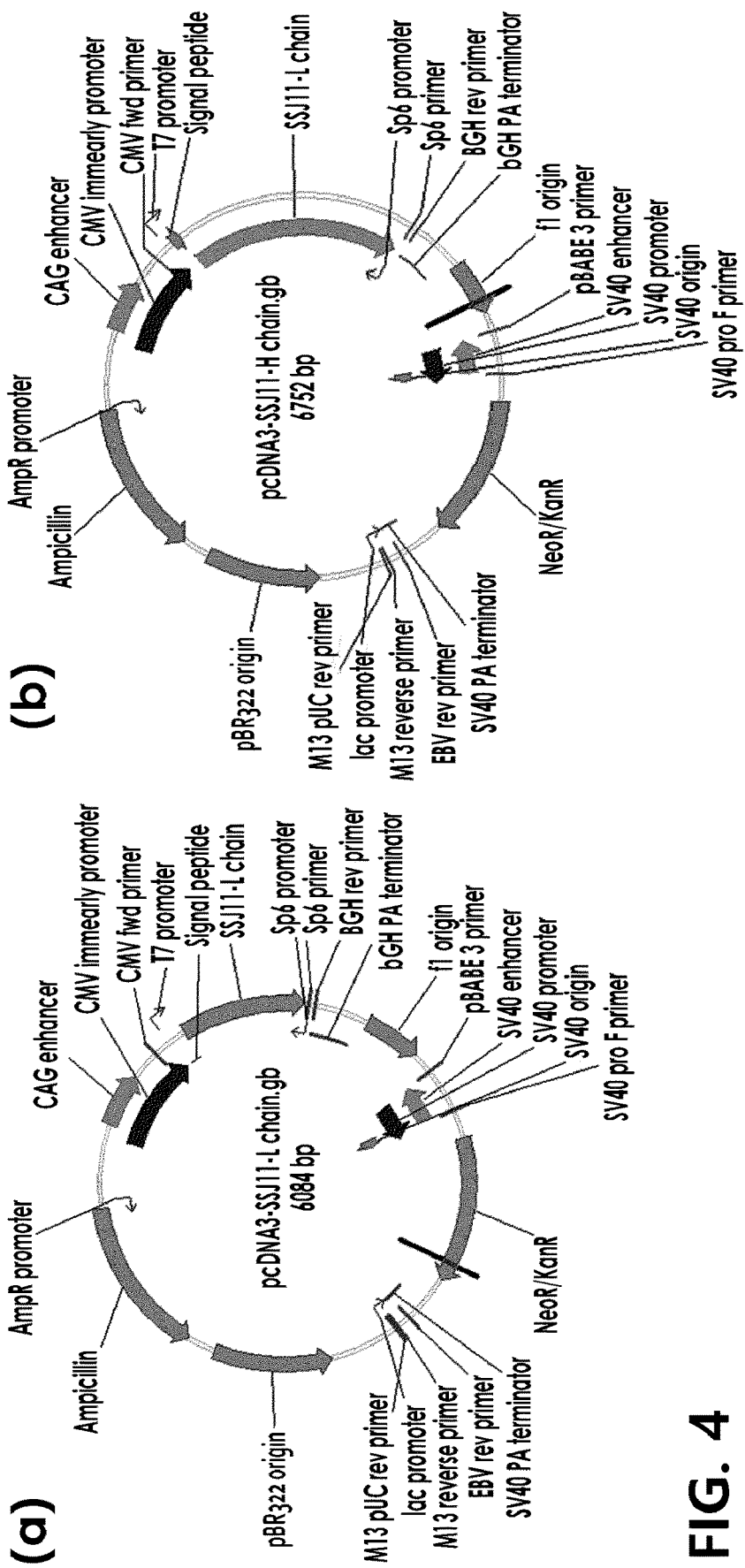
FIG. 4 shows a set of cleavage maps of a recombinant vector expressing a light chain (a) and a heavy chain (b) of a B264 antibody with high affinity.
Figure 5:
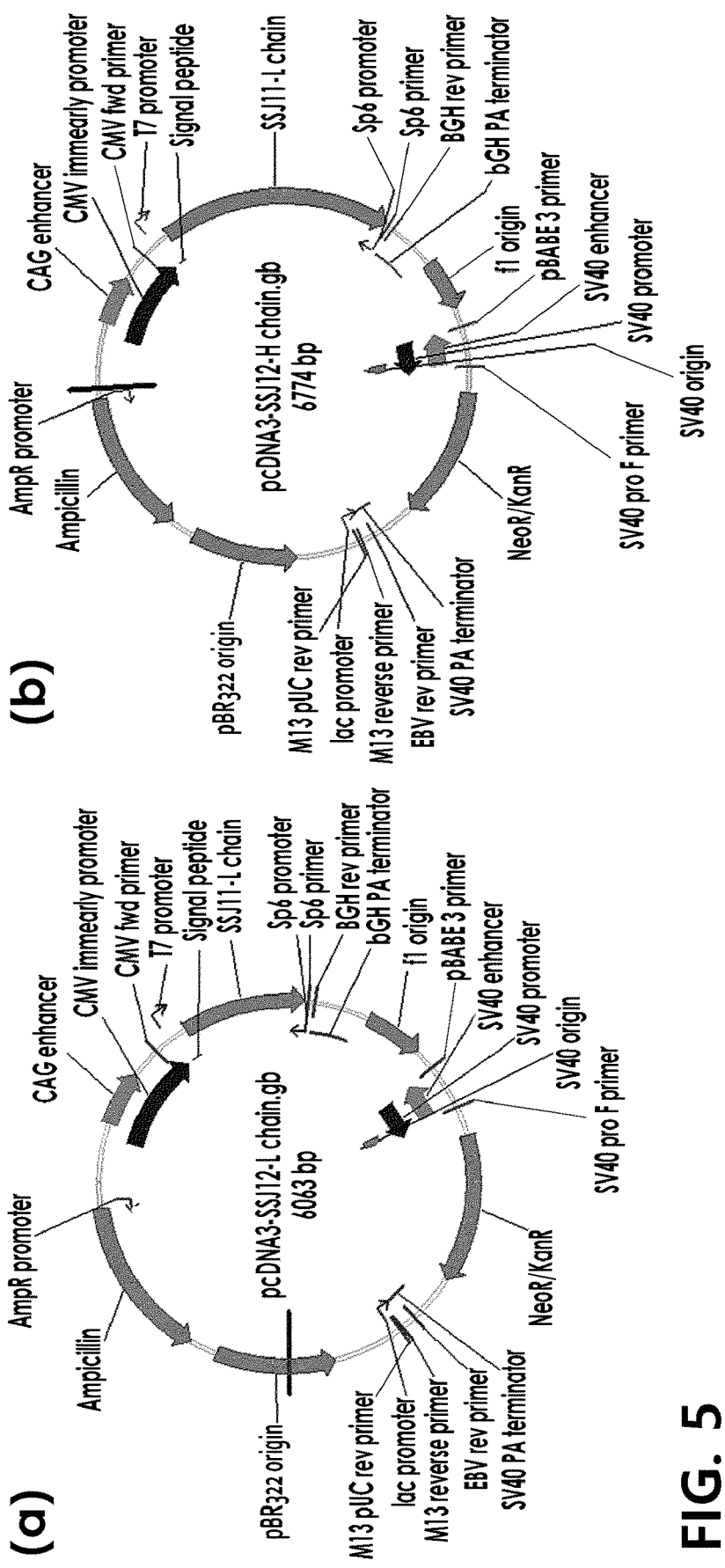
FIG. 5 shows a set of cleavage maps of a recombinant vector expressing a light chain (a) and a heavy chain (b) of a B266 antibody with high affinity.

Hereinafter, the present invention will be described in further detail.

As described above, the inventors confirmed through previous research that thioredoxin-1 is expressed in normal breast tissue at a low level, but expressed in breast cancer tissue at a very high level. Therefore, it is proved that thioredoxin-1 is useful as a marker for breast cancer diagnosis.

Therefore, through further research, the inventors developed a monoclonal antibody which very specifically binds to thioredoxin-1 and is useful in screening a breast cancer patient. The monoclonal antibody of the present invention very specifically binds to thioredoxin-1 due to excellent binding affinity to thioredoxin-1 and has very high sensitivity and specificity, such that it can be effectively used in screening a breast cancer patient. Further, the detection of thioredoxin-1 using the monoclonal antibody of the present invention, which specifically binds to thioredoxin-1, rather than the detection of CA15-3, which is another, conventionally used biomarker for breast cancer diagnosis, exhibits excellent sensitivity and specificity, such that the accuracy and reliability of the diagnosis of breast cancer can be significantly increased.

The present invention provides a monoclonal antibody binding to thioredoxin-1 (Trx1) or an antigen-binding fragment thereof.

The monoclonal antibody of the present invention may be prepared using a variety of methods known in the art such as hybridoma, recombination and phage display technologies, and a combination method thereof. For example, the monoclonal antibody may be prepared using a hybridoma technique, which is known in the art. The term "monoclonal antibody" used herein is not limited to an antibody produced using a hybridoma technique. The term "monoclonal antibody" refers to an antibody derived from a single clone of any eukaryote, prokaryote, or a phage clone, but does not refer to a method of producing the same.

A method of producing and screening a specific antibody using a hybridoma technique is common and well known in the art. As a non-limited example, a mouse can be immunized with a target antigen or cells expressing the same. When the immune reaction is detected, for example, an antibody specific to the antigen is detected from a mouse serum, a mouse spleen is collected to isolate spleen cells. Subsequently, the spleen cells are fused with any suitable myeloma cells, for example, P3U1, P3X63-Ag8, P3X63-Ag8-U1, P3NS1-Ag4, SP2/0-Ag14, or P3X63-Ag8-653 by a known method. A hybridoma is selected, and cloned by limiting dilution. Afterward, the hybridoma clone is evaluated for its ability to be a cell secreting an antibody capable of binding to an antigen by a method known in the art. Generally, ascites containing a high level of antibodies may be prepared by injecting positive hybridoma clones into the abdominal cavity of a mouse. In an exemplary embodiment of the present invention, a Trx1 antigen is prepared by transfecting E. coli with a recombinant vector having the cleavage map of FIG. 1(a). Afterward, the spleen of a rat immunized with the antigen is separated, and cells fused with myeloma cells (sp2/0) to produce an antibody reacting with Trx1 are identified by ELISA.

The exemplary monoclonal antibody of the present invention or antigen-binding fragment thereof may include (a) or (b) as follows, which may be referred to as B264 or B266-1, respectively:

(a) a light chain variable region including a light chain CDR1 consisting of the amino acid sequence of SEQ ID NO: 4, a light chain CDR2 consisting of the amino acid sequence of SEQ ID NO: 5 and a light chain CDR3 consisting of the amino acid sequence of SEQ ID NO: 6, and a heavy chain variable region; or (b) a light chain variable region including a light chain CDR1 consisting of the amino acid sequence of SEQ ID NO: 1, a light chain CDR2 consisting of the amino acid sequence of SEQ ID NO: 2 and a light chain CDR3 consisting of the amino acid sequence of SEQ ID NO: 3, and a heavy chain variable region including a heavy chain CDR1 consisting of the amino acid sequence of SEQ ID NO: 7, a heavy chain CDR2 consisting of the amino acid sequence of SEQ ID NO: 8 and a heavy chain CDR3 consisting of the amino acid sequence of SEQ ID NO: 9.

The term "complementarity-determining region (CDR)" used herein refers to the amino acid sequence of a hypervariable region of the heavy chain or light chain in an immunoglobulin. Each of heavy chains (CDRH1, CDRH2 and CDRH3) and light chains (CDRL1, CDRL2 and CDRL3) has three CDRs, and these CDRs provide key contact residues when an antibody binds to an antigen or epitope.

The exemplary monoclonal antibody of the present invention or antigen-binding fragment thereof may include (c) or (d) as follows, and may be referred to as B264 or B266-1, respectively:

(c) a light chain variable region consisting of the amino acid sequence of SEQ ID NO: 11 and a heavy chain variable region; or (d) a light chain variable region consisting of the amino acid sequence of SEQ ID NO: 10 and a heavy chain variable region consisting of the amino acid sequence of SEQ ID NO: 12.

The exemplary monoclonal antibody of the present invention or antigen-binding fragment thereof may include (e) or (f) as follows, which may be referred to as B264 or B266, respectively:

(e) a light chain consisting of the amino acid sequence of SEQ ID NO: 15 and a heavy chain consisting of the amino acid sequence of SEQ ID NO: 16; or (f) a light chain consisting of the amino acid sequence of SEQ ID NO: 13 and a heavy chain consisting of the amino acid sequence of SEQ ID NO: 14.

The exemplary monoclonal antibody of the present invention is referred to as B264, B265, B266, B267, B268 or B269, and most preferably B264 or B266-1. B266-1 is a monoclonal antibody in which the Fc part of B266 is modified to human IgG1.

The structural unit of a naturally-occurring antibody generally includes a tetramer. The tetramer is generally composed of two pairs of identical polypeptide chains, and each pair has one full-length light chain (generally having a molecular weight of about 15 kDa) and one full-length heavy chain (generally having a molecular weight of about 50 to 70 kDa). The amino end of each of the light chain and heavy chain generally includes a variable region with about 100 to 110 or more amino acids, involved in antigen recognition. The carboxyl end of each chain defines a constant region generally involved in the function of an effector. A human light chain is generally classified into κ and λ light chains. A heavy chain is generally classified into μ, δ, γ, α and ε heavy chains, which define isotypes of an antibody, such as IgM, IgD, IgG, IgA and IgE, respectively. IgG has, but is not limited to, some subclasses including IgG1, IgG2, IgG3 and IgG4. IgM has, but is not limited to, subclasses including IgM1 and IgM2. Similarly, IgA is, but is not limited to, classified into subclasses including IgA1 and IgA2. In the full-length light and heavy chains, generally, variable and constant regions are connected by a "J" region with about 12 or more amino acids, and the heavy chain also includes a "D" region with about 10 or more amino acids. A variable region of each light chain/heavy chain pair generally forms an antigen-binding site. According to an exemplary embodiment of the present invention, in the monoclonal antibody of the present invention, the heavy chain may be an IgG1, IgG2a, IgG2b, IgG3, IgA or IgM isotype, and the light chain may be a κ chain or a λ chain, and preferably, a κ light chain and an IgG1 heavy chain.

In the monoclonal antibody of the present invention or antigen-binding fragment thereof, the "antigen-binding fragment thereof" means a fragment having an antigen-binding function, and includes Fab, F(ab'), F(ab')$_2$, Fv or a single-chain antibody molecule. Among the antibody-binding fragments, Fab is a structure having light and heavy chain variable regions and a light chain constant region and the first constant region (CH1) of a heavy chain, and includes one antigen-binding site. F(ab') is different from Fab in that it has a hinge region including one or more cysteine residues at the C-terminus of the heavy chain CH1 domain. F(ab')$_2$ is formed by a disulfide bond between cysteine residues in a hinge region of Fab'. Fv is the smallest antibody fragment only having a heavy chain variable region and a light chain variable region. Such an antibody fragment may be obtained using a protease, preferably gene recombination technology. For example, Fab may be obtained by, for example, digestion of the total antibody with papain, and a F(ab')$_2$ fragment may be obtained by digestion of the total antibody with pepsin.

The exemplary antibody of the present invention may be a chimeric antibody, a humanized antibody or a complete human antibody.

The chimeric antibody may be prepared by combining variable light chain and heavy chain (VL and VH) domains obtained from one type of antibody-producing cells and constant light chain and heavy chain domains obtained from another type of antibody using a recombination means. Generally, the chimeric antibody uses a rodent or rabbit variable domain and a human constant domain to produce an antibody usually having a human domain. The production of such a chimeric antibody is widely known in the art, and may be achieved by a standard means. It is further considered that the human constant region of the chimeric antibody of the present invention can be selected from an IgG1, IgG2, IgG3, IgG4, IgG5, IgG6, IgG7, IgG8, IgG9, IgG10, IgG11, IgG12, IgG13, IgG14, IgG15, IgG16, IgG17, IgG18 or IgG19 constant region.

The humanized antibody is engineered to contain an immunoglobulin domain further more similar to a human, and includes a complementarity-determining region of an animal-derived antibody. This is achieved by closely examining the sequence of a hypervariable loop of the variable region in a monoclonal antibody, and adapting the sequence to the structure of the human antibody chain.

The complete human antibody is an antibody molecule which includes CDRs such that the total sequences of both of a light chain and a heavy chain are derived from a human gene.

The present invention also provides a nucleic acid molecule(s) encoding a heavy chain and/or a light chain of a monoclonal antibody of the present invention or an antigen-binding fragment thereof.

The term "nucleic acid molecule" used herein encompasses DNA (gDNA and cDNA) and RNA molecules, and in the nucleic acid molecule, a nucleotide, which is a basic unit, also includes an analogue in which a sugar or base part is modified, as well as a natural nucleotide. The sequences of nucleic acid molecules encoding the heavy chain and light chain variable regions of the present invention may be modified. The modification includes additions, deletions, or non-conservative or conservative substitutions of nucleotides.

The nucleic acid molecule of the present invention is interpreted to also include a nucleotide sequence having substantial identity to the nucleotide sequence described above. The substantial identity refers to a nucleotide sequence exhibiting at least 80% homology, at least 90% homology in one specific example, or at least 95% homology in another specific example when the nucleotide sequence of the present invention is aligned to correspond to a different sequence as much as possible, and the aligned sequence is analyzed using an algorithm generally used in the art.

According to an exemplary embodiment of the present invention, the nucleic acid molecule encoding a light chain of the monoclonal antibody of the present invention may consist of the nucleotide sequence of SEQ ID NO: 17, and the nucleic acid molecule encoding a heavy chain of the monoclonal antibody of the present invention may consist of the nucleotide sequence of SEQ ID NO: 18.

According to another exemplary embodiment of the present invention, the nucleic acid molecule encoding a heavy chain of the monoclonal antibody of the present invention may consist of the nucleotide sequence of SEQ ID NO: 19, and the nucleic acid molecule encoding a light chain of the monoclonal antibody of the present invention may consist of the nucleotide sequence of SEQ ID NO: 20.

The present invention also provides a recombinant vector, which includes the nucleic acid molecule encoding a heavy chain, the nucleic acid molecule encoding a light chain in the monoclonal antibody, or both of the nucleic acid molecules.

The recombinant vector system of the present invention may be constructed by various methods known in the art. The vector of the present invention may be typically constructed as a vector for cloning or a vector for expression. In addition, the vector of the present invention may be constructed using prokaryotic or eukaryotic cells as a host. For example, the vector of the present invention is an expression vector, and when prokaryotic cells are used as a host, the vector generally includes a potent promoter capable of performing transcription (e.g., a tac promoter, a lac promoter, a lacUV5 promoter, a lpp promoter, a pLk promoter, a pRk promoter, a rac5 promoter, an amp promoter, a recA promoter, an SP6 promoter, a trp promoter or a T7 promoter), a ribosome-binding site for the initiation of translation and transcription/translation termination sequences. When *E. coli* (e.g., HB101, BL21, DH5α, etc.) is used as a host cell, promoter and operator regions of an *E. coli* tryptophan biosynthesis pathway, and a pLλ promoter may be used as regulatory regions. When *Bacillus* is used as a host cell, the promoter of a toxic protein gene of *Bacillus thuringiensis* or any promoter capable of being expressed in *Bacillus* may be used as a regulatory region.

Meanwhile, the recombinant vector of the present invention may be manufactured by manipulating a plasmid used in the art (e.g., pCL, pSC101, pGV1106, pACYC177, ColE1, pKT230, pME290, pBR322, pUC8/9, pUC6, pBD9, pHC79, pIJ61, pLAFR1, pHV14, pGEX series, pET series or pUC19), a phage (e.g., λgt4·λB, λ-Charon, λΔz1 or M13) or a virus (e.g., SV40).

When the vector of the present invention is an expression vector and eukaryotic cells are used as a host, the vector generally has a promoter derived from the genome of mammalian cells (e.g., a metallothionine promoter, a β-actin promoter, a human hemoglobin promoter or a human muscle creatine promoter) or a promoter derived from a mammalian virus (e.g., an adenovirus late promoter, a vaccinia virus 7.5K promoter, SV40 promoter, a cytomegalovirus (CMV) promoter, a tk promoter of HSV, a mouse mammary tumor virus (MMTV) promoter, an LTR promoter of HIV, a Moloney virus promoter, an Epstein-Barr virus (EBV) promoter or a Rous sarcoma virus (RSV) promoter), and a polyadenylation sequence as a transcription termination sequence.

The recombinant vector of the present invention may be fused with a different sequence to facilitate the purification of an antibody expressed from the recombinant vector. The fused sequence may be, for example, a glutathione S-transferase (Amersham Pharmacia Biotech, USA); a maltose-binding protein (NEB, USA); FLAG (IBI, USA); a tag sequence such as 6×His (hexahistidine; Qiagen, USA), Pre-S1 or c-Myc; or a leading sequence such as ompA or pelB. In addition, since a protein expressed from the vector of the present invention is an antibody, the expressed antibody may be easily purified using a protein A column without an additional sequence for purification.

Meanwhile, the recombinant vector of the present invention includes an antibiotic-resistant gene generally used in the art as a selective marker, for example, a gene resistant to ampicillin, gentamicin, carbenicillin, chloramphenicol, streptomycin, kanamycin, geneticin, neomycin or tetracycline.

The vector expressing an antibody of the present invention may be a vector system expressing both of a light chain and a heavy chain using one vector, or a vector system respectively expressing a light chain and a heavy chain using two vectors. In the latter, two vectors are introduced into host cells through co-transformation and targeted transformation. The co-transformation is a method of selecting cells expressing both a light chain and a heavy chain after vector DNAs respectively encoding the light chain and the heavy chain are introduced into host cells. Targeted transformation is a method of selecting cells transformed by a vector including a light chain (or a heavy chain), transforming the selected cells expressing the light chain by a vector including a heavy chain (or a light chain), and finally selecting cells expressing both of the light chain and the heavy chain.

The present invention also provides host cells including a recombinant vector of the present invention. The host cells are cells transformed with the recombinant vector of the present invention. Host cells capable of stably and continuously cloning and expressing the vector of the present invention may be any host cells known in the art, and include prokaryotic host cells, for example, *Bacillus* sp. strains such as *Escherichia coli, Bacillus subtilis* and *Bacillus thuringiensis, Streptomyces, Pseudomonas* (e.g., *Pseudomonas putida*), *Proteus mirabilis* or *Staphylococcus* (e.g., *Staphylococcus carnosus*), but the present invention is not limited thereto.

As eukaryotic host cells suitable for the vector, multicellular fungi such as *Aspergillus* sp. strains belonging to the Phylum Ascomycota and *Neurospora crassa*, and unicellular fungi including enzymes such as yeasts such as *Pichia pastoris, Saccharomyces cerevisiae* and *Schizosaccharomyces*, other low eukaryotic cells, high eukaryotic cells such as insect-derived cells, and cells derived from a plant or mammal may be used.

The term "transfection" used herein refers to introduction of a gene of interest into host cells using the recombinant vector of the present invention, and is used with the same meaning as "transformation." Therefore, the "transfection" and/or "transformation" into host cells may be performed by suitable standard technology known in the art according to host cells, including methods of introducing a nucleic acid into an organism, cells, tissue or an organ. Such methods include electroporation, protoplast fusion, calcium phosphate ($CaPO_4$) precipitation, calcium chloride ($CaCl_2$) precipitation, stirring using a silicon carbide fiber, agrobacteria-mediated transformation, PEG, dextran sulfate, Lipofectamine and drying/inhibition-mediated transformation, but the present invention is not limited thereto.

The present invention also provides a method of preparing a monoclonal antibody specifically binding to thioredoxin-1 or an antigen-binding fragment thereof, which includes culturing the host cells.

The culture of host cells to prepare an antibody or antigen-binding fragment thereof may be performed in a suitable medium known in the art under culture conditions. The culture process may be easily adjusted according to a strain by one of ordinary skill in the art. Cell culture is classified by suspension culture or attachment culture depending on a growth method, and batch culture, fed-batch culture or continuous culture according to a culture method. The medium used in culture has to suitably satisfy requirements for specific strains.

The medium used in animal cell culture includes various carbon sources, nitrogen sources, and trace elements. Examples of carbon sources used herein may be carbohydrates such as glucose, sucrose, lactose, fructose, maltose, starch and cellulose, lipids such as soybean oil, sunflower oil, castor oil and coconut oil, fatty acids such as palmitic acid, stearic acid and linoleic acid, alcohols such as glycerol and ethanol, and organic acids such as acetic acid. These carbon sources may be used independently or in combination. Examples of nitrogen sources used herein include organic nitrogen sources such as peptones, yeast extracts, beef stock, malt extracts, corn steep liquor (CSL) and soybean powder, and inorganic nitrogen sources such as urea, ammonium sulfate, ammonium chloride, ammonium phosphate, ammonium carbonate and ammonium nitrate. These nitrogen sources may be used independently or in combination. The medium may include potassium dihydrogen phosphate, dipotassium hydrogen phosphate and a corresponding sodium-containing salt as a phosphorus source. In addition, the medium may contain a metal salt such as magnesium sulfate or iron sulfate. In addition, an amino acid, a vitamin, and a suitable precursor may be included.

During culture, compounds such as ammonium hydroxide, potassium hydroxide, ammonia, phosphoric acid and sulfuric acid may be added to a cell culture by a suitable method to adjust a pH of the cell culture. In addition, the generation of bubbles may be inhibited using a foaming agent such as fatty acid polyglycol ester during culture. In addition, to maintain an aerobic condition of the cell culture, oxygen or an oxygen-containing gas (e.g., air) is injected into the cell culture. The temperature of the cell culture is generally 20 to 45° C., and preferably 25 to 40° C.

The antibody obtained by culturing host cells may be used without purification, or may be used by purification with high purity using various conventional methods, for example, dialysis, salt precipitation, and chromatography. Among these methods, chromatography is most widely used, and the types and order of columns may be selected for ion exchange chromatography, size exclusion chromatography, or affinity chromatography according to the characteristic of an antibody or a culture method.

The present invention provides a breast cancer diagnostic kit which includes the monoclonal antibody of the present invention or antigen-binding fragment thereof, and a method of providing information necessary for breast cancer diagnosis using the same.

The term "diagnosis" used herein refers to confirmation of the presence or feature of a pathological state. For the purpose of the present invention, diagnosis is to confirm whether breast cancer occurs or not.

The thioredoxin-1 protein is a breast cancer diagnostic marker, and highly expressed in breast cancer tissue, compared with normal breast tissue.

According to an exemplary embodiment of the present invention, the breast cancer diagnostic kit may be an enzyme linked immunosorbent assay (ELISA) kit, and preferably, one or more selected from the group consisting of direct ELISA, indirect ELISA, direct sandwich ELISA and indirect sandwich ELISA. In an exemplary embodiment of the present invention, two types of antibodies included in the sandwich ELISA kit include a monoclonal antibody B266-1 as a coating antibody, and a monoclonal antibody B264 as a detection antibody.

The breast cancer diagnostic kit of the present invention may further include a tool or reagent known in the art, which is used in immunological analysis, in addition to an antibody against Trx1.

Here, the immunological analysis may be carried out with any of the methods capable of measuring the binding of an antibody to an antigen. Such methods are known in the art include, for example, western blotting, ELISA, radioimmunoprecipitation, radial immunodiffusion, an immunofluorescence assay, immunoblotting, Ouchterlony immunodiffusion, rocket immunoelectrophoresis, immunohistochemical staining, an immunoprecipitation assay, a complement fixation assay, an immunochromatographic assay, FACS, and a protein chip assay, but the present invention is not limited thereto.

As a tool or reagent used in immunological analysis, a suitable carrier or support, a marker capable of producing a detectable signal, a solubilizer, a cleaning agent, or a stabilizer may be included. When a marker is an enzyme, suitable carriers include a substrate capable of measuring enzyme activity, a suitable buffer solution, a secondary antibody labeled with a chromogenic enzyme or a fluorescent material, a chromogenic substrate or a reaction stopping agent, but the present invention is not limited thereto.

The antibody against Trx1 included in the kit of the present invention is preferably fixed to a suitable carrier or support using various methods disclosed in a document, and examples of suitable carriers and supports include PBS, polystyrene, polyethylene, polypropylene, polyester, polyacrylonitrile, a fluorine resin, agarose, cellulose, nitrocellulose, dextran, Sephadex, Sepharose, a liposome, carboxymethyl cellulose, polyacrylamide, polystyrene, gabbro, filter paper, an ion exchange resin, a plastic film, a plastic tube, a polyamine-methyl vinyl-ether-maleic acid copolymer, an amino acid copolymer, an ethylene-maleic acid copolymer, nylon, a metal, glass, a glass bead, and a magnetic particle. Other solid supports include a cell culture plate, an ELISA plate, a tube and a polymer film. The support may have any possible shape, for example, a spherical (bead), cylindrical (test tube or the inside of well), or a planar (sheet or test strip) shape.

The marker capable of producing a detectable signal is able to qualitatively or quantitatively measure the formation of an antigen-antibody complex, and may be, for example, an enzyme, a fluorescent material, a ligand, a luminous material, a microparticle, a redox molecule or a radioisotope. As an enzyme, $\beta$-glucuronidase, $\beta$-D-glucosidase, a urease, a peroxidase (e.g., horseradish peroxidase), alkaline phosphatase, acetylcholinesterase, glucose oxidase, a hexokinase, malate dehydrogenase, glucose-6-phosphate dehydrogenase, invertase, or a luciferase may be used. As a fluorescent material, fluorescein, isothiocyanate, rhodamine, phycoerythrin, phycocyanin, allophycocyanin, or fluorescein isothiocyanate may be used. As a ligand, a biotin derivative may be used, and as a luminous material, acridinium ester or a luciferin may be used. As a microparticle, colloidal gold or colored latex may be used, and as a redox molecule, ferrocene, a ruthenium complex, a viologen, a quinone, a Ti ion, a Cs ion, diimide, 1,4-benzoquinone or hydroquinone may be used. As a radioisotope, $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, or $^{186}Re$ may be used. However, other than the materials listed above, any one capable of being used in immunological analysis may be used.

As an enzyme chromogenic substrate, for example, when horseradish peroxidase (HRP) is selected as an enzyme marker, a solution containing 3-amino-9-ethylcarbazole, 5-aminosalicylic acid, 4-chloro-1-naphthol, o-phenylenediamine, 2,2'-azino-bis(3-ethylbenzothiazoline-6-sulfonic acid), 3,3-diaminobenzidine, 3,3',5,5'-tetramethylbenzidine, o-dianisidine or 3,3-dimethoxybenzidine may be used as a substrate. In addition, when an alkaline phosphatase is selected as an enzyme marker, a solution containing 5-bromo-4-chloro-3-indolyl phosphate, nitroblue tetrazolium or p-nitrophenyl phosphate may be used as a substrate. In addition, when $\beta$-D-galactosidase is selected as an enzyme marker, a solution containing o-nitrophenyl-$\beta$-D-galactoside or 5-bromo-4-chloro-3-indolyl-$\beta$-D-galactopyranoside may be used as a substrate. Other than these, various enzymes and enzyme chromogenic substances, which are known in the art, may be used.

According to an exemplary embodiment of the present invention, the method of providing information necessary for breast cancer diagnosis of the present invention may be performed with the following steps:

(a) bringing any one type of monoclonal antibody of the present invention or antigen-binding fragment thereof into contact with a biological sample isolated from a subject suspected of having breast cancer;

(b) measuring an expression level of the thioredoxin-1 protein binding to the monoclonal antibody or an antigen-binding fragment thereof in the biological sample through the formation of an antigen-antibody complex; and (c) comparing the expression level of the thioredoxin-1 protein, measured in step (b) with that of a control and, if the protein expression level is higher than that of the control, determining the subject to be a breast cancer patient.

According to another exemplary embodiment of the present invention, the method of providing information necessary for breast cancer diagnosis of the present invention may be performed with the following steps:

(a) coating a solid support with the monoclonal antibody or an antigen-binding fragment thereof of claim 2, 4 or 6;

(b) applying a biological sample isolated from a subject suspected of having breast cancer to the coated solid support;

(c) removing an unbound sample;

(d) applying the monoclonal antibody or an antigen-binding fragment thereof of claim 1, 3 or 5 to the solid support;

(e) removing an unbound monoclonal antibody or an antigen-binding fragment thereof;

(f) measuring an expression level of the thioredoxin-1 protein; and (g) comparing the expression level of the thioredoxin-1 protein, measured in step (f), with that of a control, and, if the protein expression level is higher than that of the control, determining the subject to be a breast cancer patient.

The term "isolated biological sample" used herein includes tissue (breast tissue), cells (breast cells), whole blood, plasma, serum, blood, saliva, synovial fluid, urine, sputum, lymphatic fluid, cerebrospinal fluid, a tissue autopsy sample (brain, skin, lymph nodes, spinal cord or the like), a cell culture supernatant, or ruptured eukaryotic cells, which is different in expression level of the Trx1 protein, which is a breast cancer marker, and includes a sample derived from a primary lesion or metastatic lesion. These biological samples, which are manipulated or not manipulated, may be reacted with the monoclonal antibody of the present invention to confirm an expression level of the Trx1 protein.

The term "subject" used herein includes mammals including a cow, a pig, sheep, a chicken, a dog and a human, birds, etc., and any subject suspected of having breast cancer without limitation.

Hereinafter, the present invention will be described in detail with reference to examples to help in understanding the present invention. However, examples according to the present invention may be modified into a variety of different forms, and it should not be construed that the scope of the present invention is limited to the following examples. The examples of the present invention are provided to more completely explain the present invention to those of ordinary skill in the art.

EXAMPLES

Example 1

Preparation of Human Thioredoxin-1 (Trx1) Antigen
1-1. Preparation of Trx1 Expression Vector
A gene was synthesized based on the *E. coli* codon usage to express the gene encoding the human thioredoxin-1 protein in *E. coli*. A sequence of the synthesized human thioredoxin-1 gene is shown in Table 1 below.

TABLE 1

| | Base sequence |
|---|---|
| Trx-1 gene | ATGGTCAAACAGATCGAATCAAAAA CCGCATTTCAAGAAGCCCTGGACGC CGCTGGTGACAAACTGGTCGTGGTG GACTTTAGTGCTACCTGGTGCGGCC CGTGTAAAATGATTAAACCGTTTTT CCATAGCCTGTCTGAAAAATACAGT AACGTTATCTTTCTGGAAGTGGATG TTGATGACTGCCAGGACGTCGCGAG CGAATGCGAAGTGAAATGTATGCCG ACGTTCCAGTTTTTCAAAAAAGGTC AAAAAGTCGGTGAATTTAGCGGTGC CAACAAAGAAAAACTGGAAGCCACG ATTAACGAACTGGTG (SEQ ID NO: 25) |

A primer sequence used to amplify the human thioredoxin-1 gene is shown in Table 2 below.

TABLE 2

| hTrx1-For | TAATGGTCAAACAGATCGAATC (SEQ ID NO: 26) |
|---|---|
| hTrx1-Rev | CACCAGTTCGTTAATCGTGGTAATGAAAGCT (SEQ ID NO: 27) |

To amplify a gene for cloning in a plasmid, a polymerase chain reaction (PCR) was performed. 10 pmol of a gene synthesized as a template, 10 pmol each of primers (hTrx1-For and hTrx1-Rev), dNTPs (each 2.5 mM), Exprime taq polymerase, and a buffer solution were mixed. This solution was reacted for 35 cycles at 95° C. for 2 minutes, at 95° C. for 30 seconds, at 55° C. for 30 seconds, and at 70° C. for 20 seconds, and further reacted at 70° C. for 2 minutes, and then the reaction was terminated. The amplified gene was purified, and then to clone an EcoRV site present in the multi-cloning site (MCS) of a pUC57 plasmid, the plasmid was treated with the corresponding restriction enzyme and purified. The plasmid treated with the purified gene and the restriction enzyme, a ligase and a buffer solution were mixed and reacted. To transform *E. coli* DH5α with the plasmid, a *E. coli* DH5α competent cell line was warmed at 4° C., mixed with a plasmid-mixed solution, and reacted at 4° C. for 30 minutes. After the reaction, the cells were subjected to heat shock at 42° C. for 30 seconds, stabilized at 4° C. for 2 minutes, dispensed on a Luria-Bertani (LB) solid medium containing an antibiotic (50 ug/mL of ampicillin) for uniform absorption, and cultured at 37° C. for 16 hours or more. A plasmid having the human thioredoxin-1 gene was screened from colonies grown in the cultured medium.

1-2. Trx1 Expression and Purification
The screened plasmid having the human thioredoxin-1 gene was purified, and then to express the protein, an *E. coli* BL21 strain was transformed with the purified plasmid according to the method described above. To express the thioredoxin-1 protein from the transformed strain, the strain was cultured in an LB broth containing an antibiotic to $OD_{600}$=0.5 at 37° C., and further cultured for 3 hours by adding isopropyl β-D-thiogalactopyranoside (IPTG) so that a concentration became 1 mM. Afterward, SDS-PAGE was performed to confirm protein expression. To purify the protein, the obtained cell line was disrupted using ultrasonication and then centrifuged (12,000 rpm, 30 min, 4° C.), thereby obtaining a supernatant. A commercially available anti-thioredoxin I antibody (LF-MA0055, Abfrontier) was added to the obtained supernatant to bind to the expressed thioredoxin-1, protein A/G PLUS-agarose (sc-2003, Santa Cruz) which bound to the antibody was added to react therewith, and then centrifugation and purification were performed. Afterward, the purity and molecular weight of the resulting product were confirmed through SDS-PAGE.

Example 2

Production and Purification of Trx1-Specific Monoclonal Antibody
2-1. Immunization of Mouse
The purified human thioredoxin-1 protein was mixed with an adjuvant and then injected into a mouse (BALB/c), and the mouse blood was collected and subjected to ELISA to confirm antibody production. After two immunizations, it was confirmed that an antibody titer (1:5,000) increases properly.

2-2. Cell Fusion and Preparation of Hybridoma
A B lymphocyte was isolated from the spleen extracted from the immunized mouse, and fused with cultured myeloma cells (sp2/0). The fused cells were cultured in a medium (HAT medium) containing hypoxanthine, aminopterine and thymidine, and cells (hybridomas) in which only a myeloma cell and a B lymphocyte are fused were selectively cultured.

2-3. Selection of Hybridoma Cells Producing Trx1-Specific Monoclonal Antibody
In the obtained hybridoma cells, three types of antibodies that react with the human thioredoxin-1 protein were confirmed through ELISA. The hybridoma producing an antibody that reacts with an antigen was selected from the ELISA-positive cells using a limiting dilution method.

2-4. Production and Purification of Monoclonal Antibody
The obtained three types of hybridomas were injected into mice, and then ascites was obtained from each mouse and purified using protein A affinity chromatography. The purified antibody was identified by SDS-PAGE.

Example 3

Identification of Isotype of Monoclonal Antibody
The three antibody isotypes obtained in Example 2 were confirmed using a Rapid ELISA Mouse mAbs Isotyping Kit (Pierce, Cat. 37503).
As a result, as shown in FIG. 1(*b*), it was confirmed that the heavy chain of a monoclonal antibody 2B4 is IgG1, the heavy chain of a monoclonal antibody 8F3 is IgG12a, and the heavy chain of a monoclonal antibody 9G7 is IgG2b, and the light chains are all kappa types.

Example 4

Analyses of Amino Acid Sequences of Monoclonal Antibodies 9G7(AB1) and 2B4(AB2)

The heavy chain and light chain amino acid sequences of the monoclonal antibodies 9G7(AB1) and 2B4(AB2) of the three types of monoclonal antibodies obtained in Example 2 were analyzed. As a sequence capable of being fused with an Fc region, which is suitable for back-translation and recombination expression, an amino acid sequence was determined. The sequence determined by IMTG gap alignment was aligned, and hypermutated and complete CDR3 parts were found using a hypermutation table. The sequences were identified using accurate mass peptide maps (FIGS. 2 and 3), and hypermutation and CDR3s were confirmed using MS/MS spectra.

Example 5

Comparison of Affinity and Determination of Antibody Using ELISA

A hypermutation-available position was determined in the amino acid sequence obtained through the above-described process, and therefore, genes were synthesized by altering amino acid sequences of four types (B266, B297, B268 and B269) of 9G7(AB1) and two types (B264 and B265) of 2B4(AB2). The six types of antibodies obtained above (B264~B269) were expressed, and then affinity of each antibody to an antigen was confirmed through ELISA (the numbers after "T" in Tables 3 to 5 represent production batch numbers, respectively).

Affinities to three types of antigens, that is, naked Trx1, Fc-binding Trx1(Trx1-Fc) and His-tagged Trx1 (Trx1-His) were determined through direct ELISA, and the results are sequentially shown in Tables 3 to 5. As shown in Tables 3 to 5, B264 as IgG1(κ) and B266 as IgG2b(κ) exhibited the highest affinity to three types of antigens.

TABLE 3

Results of reactions to naked Trx1 antigens

| Antibody ID | 5000 × (OD Value) |
|---|---|
| AB264-T150514-7 | 2.0575 |
| B265-T150514-10 | 1.3225 |
| AB264-T150514-8 | 1.1635 |
| B265-T150514-9 | 0.9515 |
| B267-T150519-5 | 0.8155 |
| B269-T150519-9 | 0.735 |
| B268-T150519-8 | 0.716 |
| B268-T150519-7 | 0.670 |
| B266-T150519-3 | 0.6625 |
| B266-T150519-4 | 0.6615 |
| B269-T150519-10 | 0.626 |
| B267-T150519-6 | 0.522 |

TABLE 4

Results of reactions to Trx1-Fc antigens

| Antibody ID | 5000 × (OD Value) |
|---|---|
| AB264-T150514-7 | 1.171 |
| AB264-T150514-8 | 0.494 |
| B265-T150514-10 | 0.378 |
| B265-T150514-9 | 0.273 |
| B266-T150519-3 | 0.198 |
| B266-T150519-4 | 0.181 |
| B267-T150519-5 | 0.043 |
| B267-T150519-6 | 0.023 |
| B268-T150519-8 | 0.015 |
| B268-T150519-7 | 0.003 |
| B269-T150519-9 | 0.002 |
| B269-T150519-10 | −0.001 |

TABLE 5

Results of reactions to Trx1-His antigens

| Antibody ID | 5000 × (OD Value) |
|---|---|
| AB264-T150514-7 | 1.996 |
| B265-T150514-10 | 1.465 |
| AB264-T150514-8 | 1.142 |
| B265-T150514-9 | 1.03 |
| B267-T150519-5 | 0.857 |
| B268-T150519-8 | 0.783 |
| B269-T150519-9 | 0.77 |
| B268-T150519-7 | 0.761 |
| B269-T150519-10 | 0.717 |
| B266-T150519-3 | 0.696 |
| B266-T150519-4 | 0.667 |
| B267-T150519-6 | 0.554 |

The amino acid sequences of the antibodies B264 and B266 with high affinity are shown in Table 6 below.

TABLE 6

| | Amino acid sequence |
|---|---|
| B264 light chain | QIVLTQSPAIMSASPGEKVTMTCSASSRI SYMYWYQQKPGTSPKRWIYDTSKLASGVP ARFSGSGSGTSYSLTISTMEAEDAATYYC HQRSSYPTFGAGTKLELKRADAAPTVSIF PPSSEQLTSGGASVVCFLNNFYPKDINVK WKIDGSERQNGVLNSWTDQDSKDSTYSMS STLTLTKDEYERHNSYTCEATHKTSTSPI VKSFNRNEC (SEQ ID NO: 17) |
| B264 heavy chain | EVQLQQSGAELVKPGASVKLSCTASGFNI KDTFMHWVKQRPEQGLEWIGRIDPANGNT KYDPKFQGKATITADTSSNTAYLQLSSLT SEDTAVYYCALLQYSAMDYWGQGTSVTVS SAKTTPPSVYPLAPGCGDTTGSSVTLGCL VKGYFPESVTVTWNSGSLSSSVHTFPALL QSGLYTMSSSVTVPSSTWPSQTVTCSVAH PASSTTVDKKLEPSGPISTINPCPPCKEC HKCPAPNLEGGPSVFIFPPNIKDVLMISL TPKVTCVVVDVSEDDPDVQISWFVNNVEV HTAQTQTHREDYNSTIRVVSTLPIQHQDW MSGKEFKCKVNNKDLPSPIERTISKIKGL VRAPQVYILPPPAEQLSRKDVSLTCLVVG FNPGDISVEWTSNGHTEENYKDTAPVLDS DGSYFIYSKLNMKTSKWEKTDSFSCNVRH EGLKNYYLKKTISRSPG (SEQ ID NO: 18) |
| B266 light chain | DVLMTQTPLSLPVSLGDQASISCRSSQSI VHSNGNTYLEWYLQKPGQSPKLLIYKVSN RFSGVPDRFSGSGSGTDFTLKISRVEAED LGVYYCFQGSHVPYTFGGGTKLEIKRADA |

| | Amino acid sequence |
|---|---|
| | APTVSIFPPSSEQLTSGGASVVCFLNNFY<br>PKDINVKWKIDGSERQNGVLNSWTDQDSK<br>DSTYSMSSTLTLTKDEYERHNSYTCEATH<br>KTSTSPIVKSFNRNEC<br>(SEQ ID NO: 19) |
| B266 heavy chain | QVQLQQSGAELARPGASVKMSCKASGYTF<br>TSYTMHWVKQRPGQGLEWIGYINPTSDYT<br>NYNQKFKDKATLTADKSSSTAYMQLSSLT<br>SEDSAVYFCASEGGFLYYFDYWGQGTTLT<br>VSSAKTTPPSVYPLAPGSAAQTNSMVTLG<br>CLVKGYFPEPVTVTWNSGSLSSGVHTFPA<br>VLQSDLYTLSSSVTVPSSTWPSETVTCNV<br>AHPASSTKVDKKIVPRDCGCKPCICTVPE<br>VSSVFIFPPKPKDVLTITLTPKVTCVVVD<br>ISKDDPEVQFSWFVDDVEVHTAQTQPREE<br>QFNSTFRSVSELPIMHQDWLNGKEFKCRV<br>NSAAFPAPIEKTISKTKGRPKAPQVYTIP<br>PPKEQMAKDKVSLTCMITDFFPEDITVEW |

| | Amino acid sequence |
|---|---|
| | QWNGQPAENYKNTQPIMDTDGSYFVYSKL<br>NVQKSNWEAGNTFTCSVLHEGLHNHHTEK<br>SLSHSPGK<br>(SEQ ID NO: 20) |

Example 6

Production of Antibodies B264 and B266
6-1. Preparation of Plasmids Expressing Antibodies B264 and B266

Since the amino acid sequences of the antibodies B264 and B266 are identified as shown in Table 6, genes corresponding to the light chain and heavy chain of the respectively antibodies can be chemically synthesized. The synthesized gene sequences are shown in Table 7 below. The synthesized genes were cloned in pcDNA3.0.

TABLE 7

| | Gene sequence |
|---|---|
| B264 light chain | GACGTGCTGATGACACAGACACCACTCAGCCTCCCTGTGAGCCTGGGCGACCAGGC<br>CTCTATTTCTTGCCGGTCTAGCCAGAGCATCGTGCACTCCAACGGCAACACATACTT<br>GGAGTGGTATCTACAGAAGCCCGGCCAGTCCCCTAAGCTGCTGATATACAAGGTGT<br>CTAACCGCTTCTCCGGCGTGCCCGACAGGTTCTCTGGCAGCGGCTCTGGCACCGACT<br>TCACCCTCAAAATATCTAGGGTGGAGGCCGAGGACCTGGGCGTGTACTACTGCTTCC<br>AGGGCTCCCACGTTCCATACACATTCGGCGGCGGCACAAAGTTGGAAATTAAGCGC<br>GCTGACGCAGCCCCAACAGTGAGCATCTTTCCTCCATCCTCTGAACAACTTACCTCT<br>GGAGGAGCCTCTGTGGTGTGTTTCCTGAACAACTTCTACCCAAAGGACATCAATGTG<br>AAGTGGAAGATTGATGGCTCTGAGAGACAGAATGGAGTGCTGAACTCCTGGACAGA<br>CCAGGACAGCAAGGACAGCACCTACAGTATGAGTAGCACCCTGACCCTGACCAAGG<br>ATGAATATGAGAGACACAACTCCTACACTTGTGAGGCTACCCACAAGACCAGCACC<br>AGCCCAATTGTCAAATCCTTCAACAGGAATGAGTGTTAA<br>(SEQ ID NO: 21) |
| B264 heavy chain | CAGGTGCAGCTCCAGCAGTCCGGCGCCGAACTGGCCAGACCTGGCGCCAGCGTGAA<br>GATGAGCTGCAAGGCCTCCGGCTACACATTCACATCTTACACCATGCACTGGGTGAA<br>GCAGAGACCCGGCCAGGGCCTGGAGTGGATTGGCTACATTAACCCAACATCCGACT<br>ACACAAACTACAACCAGAAGTTCAAGGACAAGGCCACACTCACCGCCGACAAGTCT<br>TCTAGCACAGCCTACATGCAGCTGTCTAGCCTGACAAGCGAGGACTCTGCCGTGTAC<br>TTCTGCGCCTCTGAGGGCGGCTTCCTGTACTACTTCGACTACTGGGGCCAGGGCACC<br>ACCCTGACCGTGTCCTCTGCCAAAACGACACCCCCATCTGTCTATCCACTGGCCCCT<br>GGATCTGCTGCCCAAACTAACTCCATGGTGACCCTGGGATGCCTGGTCAAGGGCTAT<br>TTCCCTGAGCCAGTGACAGTGACCTGGAACTCTGGATCCCTGTCCAGCGGTGTGCAC<br>ACCTTCCCAGCTGTCCTGCAGTCTGACCTCTACACTCTGAGCAGCTCAGTGACTGTC<br>CCCTCCAGCACCTGGCCCAGCGAGACCGTCACCTGCAACGTTGCCCACCCGGCCAGC<br>AGCACCAAGGTGGACAAGAAAATTGTGCCCAGGGATTGTGGTTGTAAGCCTTGCAT<br>ATGTACAGTCCCAGAAGTATCATCTGTCTTCATCTTCCCCCCAAAGCCCAAGGATGT<br>GCTCACCATTACTCTGACTCCTAAGGTCACGTGTGTTGTGGTAGACATCAGCAAGGA<br>TGATCCCGAGGTCCAGTTCAGCTGGTTTGTAGATGATGTGGAGGTGCACACAGCTCA<br>GACGCAACCCCGGGAGGAGCAGTTCAACAGCACTTTCCGCTCAGTCAGTGAACTTC<br>CCATCATGCACCAGGACTGGCTCAATGGCAAGGAGTTCAAATGCAGGGTCAACAGT<br>GCAGCTTTCCCTGCCCCCATCGAGAAAACCATCTCCAAAACCAAAGGCAGACCGAA<br>GGCTCCACAGGTGTACACCATTCCACCTCCCAAGGAGCAGATGGCCAAGGATAAAG<br>TCAGTCTGACCTGCATGATAACAGACTTCTTCCCTGAAGACATTACTGTGGAGTGGC<br>AGTGGAATGGGCAGCCAGCGGAGAACTACAAGAACACTCAGCCCATCATGGACACA<br>GATGGCTCTTACTTCGTCTACAGCAAGCTCAATGTGCAGAAGAGCAACTGGGAGGC<br>AGGAAATACTTTCACCTGCTCTGTGTTACATGAGGGCCTGCACAACCACCATACTGA<br>GAAGAGCCTCTCCCACTCTCCTGGTAAATAA<br>(SEQ ID NO: 22) |
| B266 light chain | CAGATCGTGCTCACACAGTCTCCAGCCATCATGAGCGCCTCTCCTGGCGAGAAGGTG<br>ACAATGACCTGCTCTGCCTCTAGCCGCATTTCTTACATGTACTGGTATCAGCAGAAG<br>CCAGGCACCTCCCCTAAGAGGTGGATATACGACACATCCAAGCTGGCCTCCGGCGT<br>GCCCGCCGGTTCAGCGGCTCTGGCAGCGGCACAAGCTACTCCCTGACAATTAGCAC<br>GATGGAGGCCGAGGACGCCGCCACATACTACTGCCACCAGCGCTCGTCCTACCCAA<br>CATTCGGCGCCGGCACAAAATTGGAACTGAAGAGAGCTGACGCAGCCCCAACAGTG<br>AGCATCTTTCCTCCATCCTCTGAACAACTTACCTCTGGAGGAGCCTCTGTGGTGTGTT<br>TCCTGAACAACTTCTACCCAAAGGACATCAATGTGAAGTGGAAGATTGATGGCTCTG<br>AGAGACAGAATGGAGTGCTGAACTCCTGGACAGACCAGGACAGCAAGGACAGCAC |

TABLE 7-continued

| | Gene sequence |
|---|---|
| | CTACAGTATGAGTAGCACCCTGACCCTGACCAAGGATGAATATGAGAGACACAACT<br>CCTACACTTGTGAGGCTACCCACAAGACCAGCACCAGCCCAATTGTCAAATCCTTCA<br>ACAGGAATGAGTGTTAA<br>(SEQ ID NO: 23) |
| B266 heavy chain | GAGGTGCAGTTACAACAGTCCGGCGCCGAGCTAGTGAAGCCAGGCGCCAGCGTGAA<br>GCTGTCTTGCACAGCCAGCGGCTTCAACATTAAGGACACCTTCATGCACTGGGTGAA<br>GCAGAGACCTGAGCAGGGCTTAGAGTGGATTGGCCGGATCGACCCCGCCAACGGCA<br>ACACAAAGTACGACCCAAAGTTCCAGGGCAAGGCCACAATTACCGCCGACACATCT<br>TCCAACACAGCCTACCTCCAGCTGTCGTCTCTCACCAGCGAGGACACCGCCGTGTAC<br>TACTGCGCCCTGCTCCAGTACTCCGCGATGGACTACTGGGGCCAGGGCACATCTGTG<br>ACCGTGTCTAGCGCCAAGACCACCCCACCATCCGTGTACCCACTCGCCCCAGGCTGC<br>GGCGACACCACAGGCTCTAGCGTGACACTGGGCTGCCTGGTGAAGGGCTACTTCCC<br>CGAGTCTGTGACAGTGACCTGGAACTCTGGCTCTCTGTCTAGCTCTGTGCACACCTT<br>CCCCGCCCTGCTGCAATCCGGCCTGTACACAATGTCTTCTTCTGTGACAGTGCCTAG<br>CTCTACATGGCCATCTCAGACAGTGACATGCTCTGTGGCCCACCCCGCCTCTAGCAC<br>AACCGTGGACAAGAAGCTGGAGCCATCCGGCCCTATTTCTACAATTAACCCTTGCCC<br>TCCTTGCAAAGAATGCCACAAGTGCCCCGCCCCAAACCTGGAGGGCGGCCCTTCTGT<br>GTTCATTTTCCCTCCTAACATTAAGGACGTGCTGATGATCAGCCTCACCCCAAAGGT<br>GACATGCGTGGTGGTGGACGTGTCCGAGGACGACCCTGACGTGCAGATTTCTTGGTT<br>CGTGAACAACGTGGAGGTGCACACCGCCCAGACCCAGACCCACCGGGAGGACTACA<br>ACTCCACCATTCGGGTGGTGTCTACACTGCCTATTCAGCACCAGGACTGGATGAGCG<br>GCAAAGAGTTCAAGTGCAAGGTGAACAACAAGGACCTGCCATCTCCTATTGAGAGA<br>ACAATTTCTAAGATTAAGGGCCTGGTGCGCGCCCCTCAGGTGTACATTCTGCCTCCT<br>CCCGCCGAGCAGCTGAGCCGGAAGGACGTGTCCCTCACATGCCTCGTGGTGGGCTTC<br>AACCCTGGCGACATTAGCGTGGAGTGGACATCTAACGGCCACACAGAAGAAAACTA<br>CAAGGACACAGCCCCTGTGCTCGACTCCGACGGCTCTTACTTCATATACTCTAAGCT<br>GAACATGAAAACATCTAAGTGGGAAAAGACCGACTCTTTCTCTTGCAACGTGCGGC<br>ACGAGGGCCTGAAGAACTACTACCTCAAGAAAACCATTAGCAGAAGTCCAGGCTAA<br>(SEQ ID NO: 24) |

6-2. Expression and Purification of Antibodies B264 and B266

A HEK293 cell line was co-transfected with pcDNA3-SSJ11-L and pcDNA3-SSJ11-H to express a B264 antibody or pcDNA3-SSJ12-L and pcDNA3-SSJ12-H to express a B266 antibody, and cultured for 7 days. The cell line was cultured, and recombinant monoclonal antibodies secreted into the culture medium were collected and purified through protein A chromatography. An eluent containing the recombinant monoclonal antibodies was concentrated by ultrafiltration, and the antibodies were obtained with high purity using a 0.2-μm sterile filter.

Figure 6:
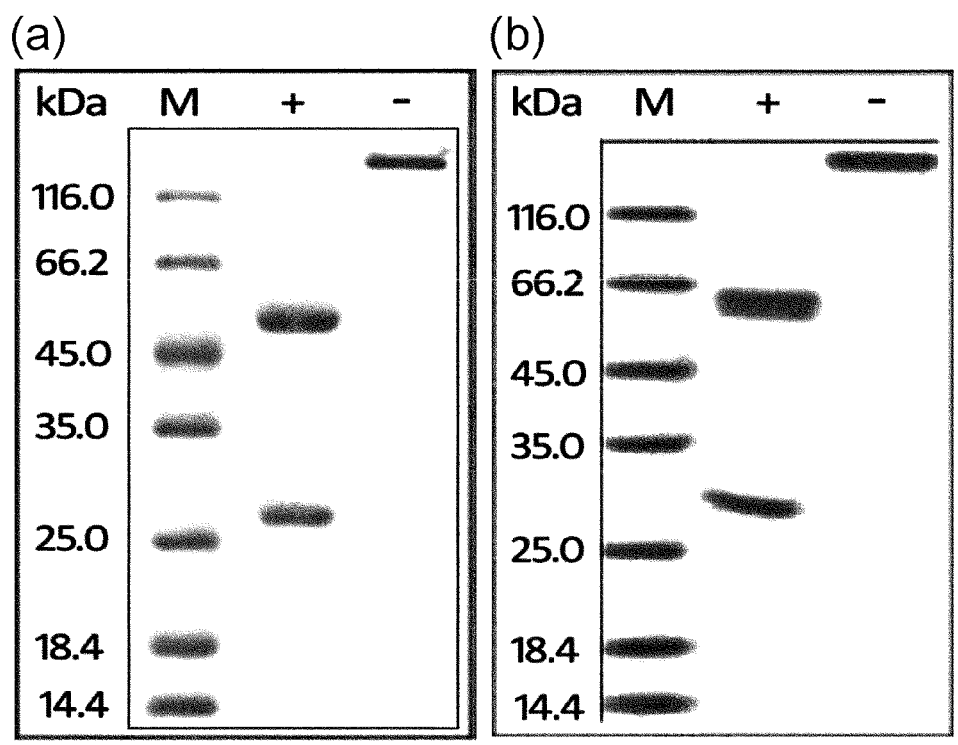
FIG. 6 shows results of identifying the reduced (+) and non-reduced (−) states of antibodies using SDS-PAGE, where (a) is the result for the antibody B264, and (b) is the result for the antibody B266.

The purity and size of the purified antibodies were determined through SDS-PAGE. As a result of SDS-PAGE, as shown in FIG. 6, it was confirmed that the antibodies B264 and B266 are expressed with sizes, for example, 47 kDa for the heavy chain and 25 kDa for the light chain under a reducing condition, and 150 kDa under a non-reducing condition, suggesting that the sizes correspond to estimated sizes.

Example 7

Confirmation of Pairing of Two Types of Monoclonal Antibodies Obtained Through Sandwich ELISA 100 μl of a coating buffer (0.015 M $Na_2CO_3$, 0.035 M $NaHCO_3$, 0.003 M $NaN_3$, pH9.6) and 100 ng of a coating antibody (B266) were mixed and dispensed to each well, and an O/N reaction was performed at 4° C. 200 μl of 1% BSA-containing PBS (PBSA; blocking buffer) per well was dispensed, and subjected to a reaction at room temperature for 60 minutes. Afterward, 20 μl of an antigen (50, 25, 12.5 or 0 ng) was dispensed, 80 μl of a detection antibody (biotin-labeled B264; B264-B) was dispensed, and the resulting mixture was reacted at 37° C. for 90 minutes. A reaction solution was removed, and washing was performed by dispensing 200 μl of PBS containing 0.05% Tween 20 (PBST; washing buffer) to each well. The above-described process was performed three times.

100 μl of streptavidin-HRP diluted 1:200 was treated in each well and reacted at 37° C. for 30 minutes. After a reaction solution was removed, washing was performed by dispensing 200 μl of PBS containing 0.05% Tween 20 (PBST; washing buffer) to each well. The above-described process was performed three times.

100 μl of a TMB solution was dispensed to each well and reacted under a dark condition at room temperature for 10 minutes, 100 μl of a 2.5M sulfuric acid solution ($H_2SO_4$; stop buffer) was treated in each well, and the result was confirmed at 450 nm.

As a result, as shown in Table 8, the reaction value increases according to the concentration of an antigen, showing the detection of the antigen by these antibodies. However, since the O.D. value is high when there is no antigen, a performance improvement experiment using an antibody is needed.

TABLE 8

| Sandwich ELISA using B266 as coating antibody and B264 as detection antibody | | | | |
|---|---|---|---|---|
| Trx1 (ng/mL) | 0 | 12.5 | 25 | 50 |
| $O.D._{450\,nm}$ | 0.828 | 1.226 | 1.506 | 2.257 |

Example 8

Alteration of Isotype of Fc Part for Improving Antibody Performance

Since the expression system of an antibody is transient transfection using a recombinant plasmid, rather than a hybridoma, among these recombinant plasmids, a plasmid having a heavy chain was co-transfected with a plasmid having a different isotype of heavy chain. That is, a plasmid having a gene encoding a different heavy chain, rather than pcDNA3-SSJ12-H of pcDNA3-SSJ12-L and pcDNA3-SSJ12-H used to express 9G7(AB1), was co-transfected.

Figure 7:
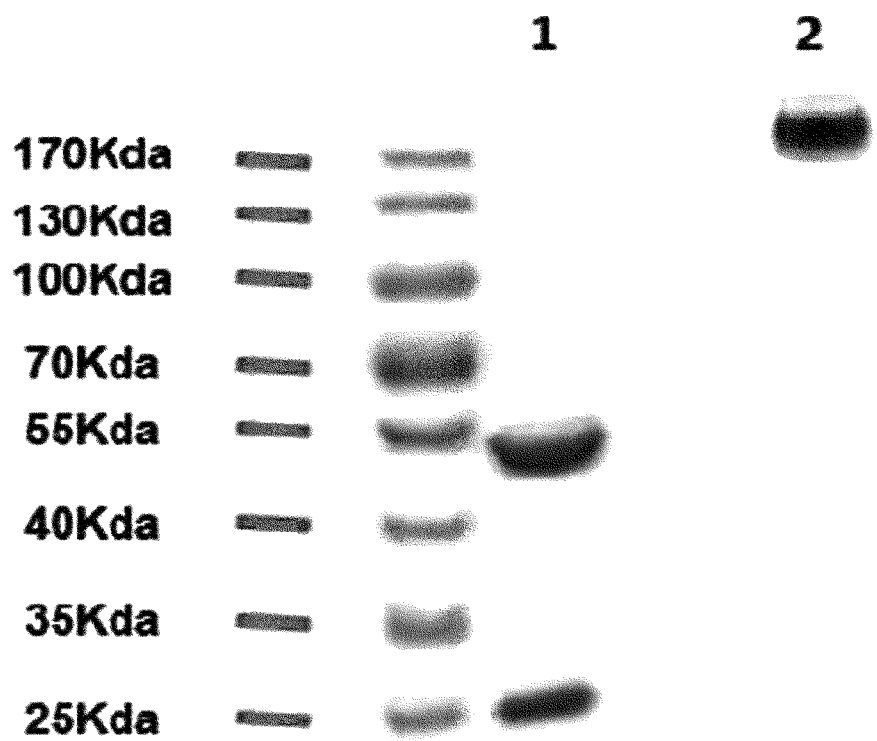
FIG. 7 shows results of identifying the reduced (+) and non-reduced (−) states of an antibody B266-1 using SDS-PAGE, in which the antibody B266-1 is prepared by modifying an Fc part of the antibody B266 to human IgG1.

An antibody (B266-1) in which the Fc part of B266 is changed to human IgG1 was obtained by the above-described method. The characteristics of the antibody were determined through SDS-PAGE (FIG. 7).

The amino acid sequences of light chains CDR1 to CDR3 and heavy chains CDR1 to CDR3 of the finally selected monoclonal antibodies B264 and B266-1 are shown in Table 9, and the amino acid sequences of the light chain variable regions and heavy chain variable regions are shown in Table 10.

TABLE 9

| | Amino acid sequence |
|---|---|
| B264 light chain CDR1 | SRISYM (SEQ ID NO: 1) |
| B264 light chain CDR2 | DTS (SEQ ID NO: 2) |
| B264 light chain CDR3 | HQRSSYP (SEQ ID NO: 3) |
| B264 heavy chain CDR1 | GFNIKDTF (SEQ ID NO: 4) |
| B264 heavy chain CDR2 | IDPANGNT (SEQ ID NO: 5) |
| B264 heavy chain CDR3 | A (SEQ ID NO: 6) |
| B266-1 light chain CDR1 | QSIVHSNGNTY (SEQ ID NO: 7) |
| B266-1 light chain CDR2 | KVS (SEQ ID NO: 8) |
| B266-1 light chain CDR3 | FQGSHVP (SEQ ID NO: 9) |
| B266-1 heavy chain CDR1 | GFNIKDTF (SEQ ID NO: 10) |
| B266-1 heavy chain CDR2 | IDPANGNT (SEQ ID NO: 11) |
| B266-1 heavy chain CDR3 | A (SEQ ID NO: 12) |

TABLE 10

| | Amino acid sequence |
|---|---|
| B264 light chain variable region | QIVLTQSPAIMSASPGEKVTMTCSA SSRISYMYWYQQKPGTSPKRWIYDT SKLASGVPARFSGSGSGTSYSLTIS TMEAEDAATYYCHQRSSYP (SEQ ID NO: 13) |
| B264 heavy chain variable region | EVQLQQSGAELVKPGASVKLSCTAS GFNIKDTFMHWVKQRPEQGLEWIGR IDPANGNTKYDPKFQGKATITADTS SNTAYLQLSSLTSEDTAVYYCA (SEQ ID NO: 14) |
| B266-1 light chain variable region | DVLMTQTPLSLPVSLGDQASISCRS SQSIVHSNGNTYLEWYLQKPGQSPK LLIYKVSNRFSGVPDRFSGSGSGTD FTLKISRVEAEDLGVYYCFQGSHVP (SEQ ID NO: 15) |
| B266-1 heavy chain variable region | EVQLQQSGAELVKPGASVKLSCTAS GFNIKDTFMHWVKQRPEQGLEWIGR IDPANGNTKYDPKFQGKATITADTS SNTAYLQLSSLTSEDTAVYYCA (SEQ ID NO: 16) |

Example 9

Confirmation of Pairing of Monoclonal Antibodies B266-1 and B264 Obtained Through Sandwich ELISA 100 µl of a coating buffer and 100 ng of a coating antibody (B266-1) were mixed and dispensed to each well, and an O/N reaction was performed at 4° C. Washing was performed by dispensing 200 µl of a washing buffer. The above-described process was performed two times.

200 µl of PBSA was dispensed to each well and reacted at room temperature for 120 minutes, and then 20 µl of an antigen (25 or 0 ng) was dispensed, 80 µl of a detection antibody (B264-B) was dispensed, and a reaction was performed at 37° C. for 90 minutes. A reaction solution was removed, and then washing was performed by dispensing 200 µl of a washing buffer to each well. The above-described process was performed three times.

100 µl of streptavidin-HRP diluted 1:200 was treated in each well, a reaction was performed at 37° C. for 30 minutes, a reaction solution was removed, and then washing was performed by dispensing 200 µl of washing buffer to each well. The above-described process was performed three times.

100 µl of a TMB solution was dispensed to each well, a reaction was performed under a dark condition at room temperature for 10 minutes, 100 µl of a stop buffer was treated in each well, and the result was confirmed at 450 nm.

As a result, as shown in Table 11, it was confirmed that the antibodies are suitably reacted with antigens, and a blank value was decreased as compared with the antibodies used in Example 6.

TABLE 11

| Sandwich ELISA using B266-1 as coating antibody and B264 as detection antibody | | | | |
|---|---|---|---|---|
| Trx1 (ng/mL) | 0 | | 25 | |
| O.D.$_{450\,nm}$ | 0.425 | 0.415 | 1.571 | 1.426 |

Example 10

Analysis of Affinity of Monoclonal Antibody to Antigen

Two types of monoclonal antibodies specifically acting on the antigen Trx1 were expressed using a transient transfection system using a plasmid, and thus stably produced. To confirm the affinity to an antigen, analysis was performed through ELISA (FIG. 8(a)).

100 µl of a coating buffer and 100 ng of Trx1 were mixed and dispensed to each well, and then reacted at 4° C. for 16 hours or more. After the reaction solution was removed, 200 µl of PBSA was dispensed to each well and reacted at 37° C. for 120 minutes. After the reaction solution was removed, the produced antibody B266-1 or B264 was diluted 1/5 from 0.1 µM, and dispensed to each well at 100 µl, and then reacted at 37° C. for 120 minutes. After the reaction solution was removed, washing was performed by dispensing 200 µl of a washing buffer to each well. The above-described process was performed two times.

100 µl of human IgG-HRP (diluted to 1:4000) as the antibody B266-1 was reacted with 100 µl of mouse IgG-HRP (diluted to 1:4000) as the antibody B264 at 37° C. for 60 minutes. After the reaction solution was removed, washing was performed by dispensing 200 µl of a washing buffer to each well. The above-described process was performed three times.

100 µl of a TMB solution was dispensed to each well, a reaction was performed under a dark condition at room temperature for 10 minutes, 100 µl of a stop buffer was treated in each well, and the result was confirmed at 450 nm. The resulting values were analyzed using Prism (Graphpad) (FIG. 8(b)).

As a result of analyzing the affinity of the coating antibody B266-1 and the detection antibody B264, it was confirmed that a blank value is high due to the reactivity of B266-1, but B266-1 and B264 are increased in binding degree according to an increased concentration of an antigen. This shows that B266-1 and B264 are bound with an antigen. When an equilibrium dissociation constant ($K_D$) value is calculated through analysis using the Prism program, the $K_D$ of B266-1 was $1.1 \times 10^{-11}$, and the $K_D$ of B264 was $1.3 \times 10^{-10}$. When the $K_D$ value is between $10^{-10}$ and $10^{-12}$, it was evaluated that the antibody has a picomole (pM) level of sensitivity to an antigen, showing that B266-1 and B264 have a high level of sensitivity to an antigen.

Example 11

Sandwich ELISA of Serum of Breast Cancer Patient

Sandwich ELISA using a coating antibody (B266-1) was prepared in a process as follows.

A 1 µg/mL coating antibody solution was prepared by adding 100 mL of a coating buffer and 0.1 mL of 1 mg/mL B266-1. 100 µl of the prepared coating antibody solution was dispensed to each well of a 96-well plate, and reacted at 4° C. for 12 hours. The antibody solution was removed, and washing was performed by dispensing 200 µl of 0.05% PBST to each well. The washing was performed three times. 200 µl of PBSA was treated in each well, and a reaction (blocking process) was performed at 4° C. for 4 hours. The PBSA was removed, and then the 96-well plate was dried in a thermo-hygrostat (20° C., 30% R.H.) for 3 hours.

Afterward, the detection antibody (B264) was biotinylated with a process as follows.

Dimethyl sulfoxide (DMSO) is mixed with 20 mg/mL biotin-7-NHS, thereby preparing 2 mg/mL biotin-7-NHS. 15 µl (30 µg) of 2 mg/mL biotin-7-NHS was added to the 1 mg/mL B264 antibody, and reacted at 15 to 25° C. for 2 hours. A reaction solution was added to AMICON ultra-15 (Millipore), filled with a PBS solution to the final volume, and centrifuged at 3,600×g until it remained at 0.5 mL. The process was performed three times. The antibody solution (biotinylated B264; B264-B) remaining in the AMICON filter was transferred to a 1.5 mL tube, and filled with PBSA to the final concentration of 0.3 mg/mL.

Subsequently, human Trx1 antigen detection from the serum of a breast cancer patient was performed as follows.

A standard antigen solution was dispensed to the first column of a 96-well plate coated with a coating antibody. 20 µl of the serum obtained from a breast cancer was dispensed, and then 80 µl (0.3 mg/mL) of a B264-B solution was dispensed. Afterward, after a reaction at 37° C. for 60 minutes, an antigen-antibody reaction solution was removed, and then washing was performed by dispensing 200 µl of PBST to each well. The washing process was performed three times. 100 µl of a 1:400-dilution of streptavidin-HRP (R&D Systems) was dispensed, and a reaction was performed at 37° C. for 30 minutes. After the reaction, a reaction solution was removed, and washing was performed by dispensing 200 µl of PBST to each well. The washing process was performed three times. 100 µl of a TMB solution (Sure Blue) was treated, and a reaction was performed at room temperature for 15 minutes under a dark condition. 100 µl of a 2N $H_2SO_4$ solution was dispensed, and an absorbance was measured at 450 nm using a microplate reader.

Finally, ROC analysis was performed as follows.

Figure 9:
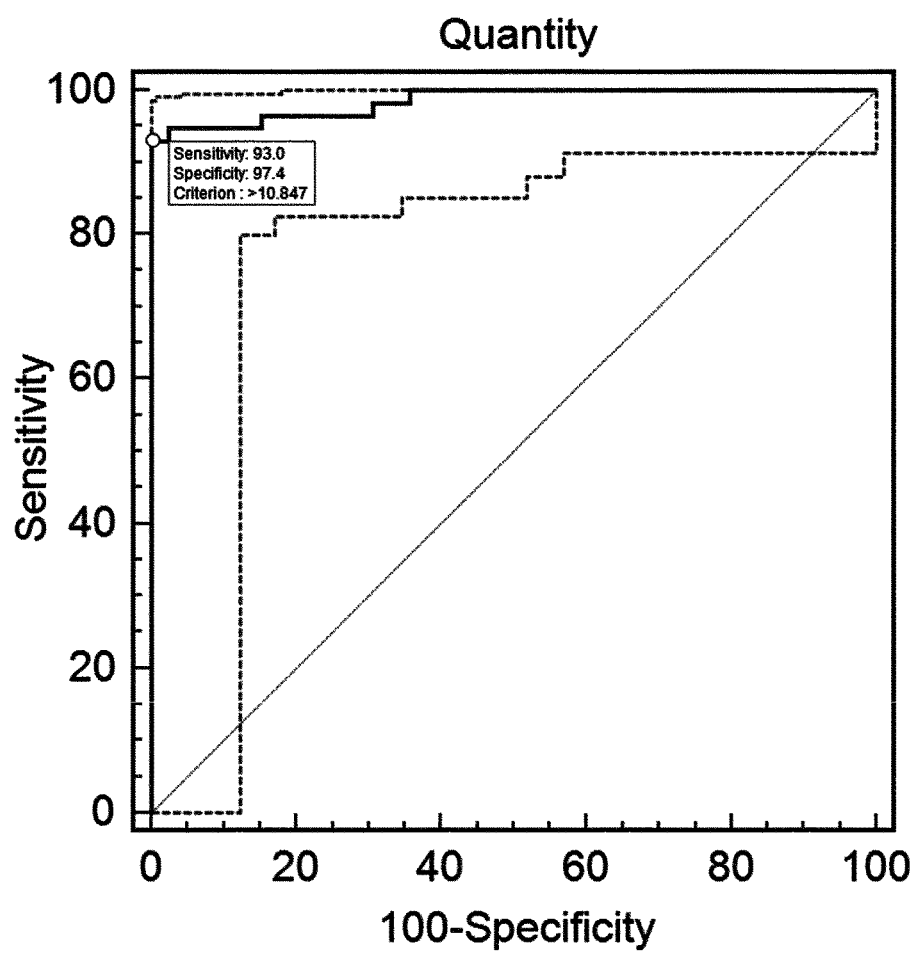
FIG. 9 is a graph showing sensitivity and specificity through ROC analysis of ELISA results using the antibody B266-1 and the antibody B264.

Sensitivity and specificity were calculated by analyzing a result of ELISA using monoclonal antibodies B266-1 and B264 against Trx1. When a cut-off value was 10.8 ng/mL, the sensitivity was 93.0%, and the sensitivity was 97.4% (FIG. 9).

Example 12

Comparative Analysis with Another ELISA Kit for Breast Cancer Diagnosis

In this example, to evaluate the performance of recombinant monoclonal antibodies B266-1 and B264, another ELISA kit for detecting another biomarker CA15-3 for breast cancer diagnosis was comparatively analyzed (Table 12).

As a result, as shown in Table 12, when a monoclonal antibody specifically binding to Trx1 is used, sensitivity and specificity were exceptionally higher than those of CA15-3.

TABLE 12

Comparison of kit of the present invention with AxSYM CA15-3 kit

|  | Ttx1 | CA15-3 (AxSYM) |
|---|---|---|
| Sensitivity (%) | 93 | 54 |
| Specificity (%) | 97.4 | 94 |
| Test sample | Serum | Serum and plasma |

A monoclonal antibody of the present invention has excellent binding affinity to thioredoxin-1, thereby very specifically binding to thioredoxin-1, and has very high sensitivity and specificity, thereby being effectively used in screening a breast cancer patient. Further, detection of thioredoxin-1 using the monoclonal antibody specifically binding to thioredoxin-1 of the present invention, rather than detection using a conventional breast cancer diagnostic biomarker CA15-3, exhibits exceptionally high sensitivity and specificity, and thus the accuracy and reliability of breast cancer diagnosis can be significantly increased, suggesting that the monoclonal antibody of the present invention has high industrial availability.

The invention claimed is:

1. A monoclonal antibody specifically binding to thioredoxin-1 or an antigen-binding fragment thereof, comprising:
(i) a light chain variable region consisting of the amino acid sequence of SEQ ID NO: 11 and a heavy chain consisting of the amino acid sequence of SEQ ID NO: 16; or
(ii) a light chain variable region consisting of the amino acid sequence of SEQ ID NO: 10 and a heavy chain variable region consisting of the amino acid sequence of SEQ ID NO: 12.

2. The monoclonal antibody or antigen-binding fragment thereof according to claim 1, wherein the antibody comprises:
(i) a light chain consisting of the amino acid sequence of SEQ ID NO: 15 and a heavy chain consisting of the amino acid sequence of SEQ ID NO: 16; or
(ii) a light chain consisting of the amino acid sequence of SEQ ID NO: 13 and a heavy chain consisting of the amino acid sequence of SEQ ID NO: 14.

3. The monoclonal antibody or antigen-binding fragment thereof according to claim 1, wherein the antibody comprises an IgG1 heavy chain and a kappa (κ) light chain.

4. The monoclonal antibody or antigen-binding fragment thereof according to claim 1, wherein the antigen-binding fragment is Fab, F (ab'), F (ab')$_2$, Fv or a single-chain antibody molecule.

5. The monoclonal antibody or antigen-binding fragment thereof according to claim 1, wherein the antibody is a chimeric antibody or a humanized antibody.

6. A nucleic acid molecule encoding a light chain or a heavy chain of the monoclonal antibody or antigen-binding fragment thereof according to claim 1.

7. The nucleic acid molecule according to claim 6, wherein the nucleic acid molecule encoding the light chain consists of the nucleotide sequence of SEQ ID NO: 17 or SEQ ID NO: 19 and the nucleic acid molecule encoding the heavy chain consists of the nucleotide sequence of SEQ ID NO: 18 or SEQ ID NO: 20.

8. A breast cancer diagnostic kit comprising the monoclonal antibody or antigen-binding fragment thereof of claim 1.

9. The breast cancer diagnostic kit according to claim 8, wherein the kit is an enzyme linked immunosorbent assay (ELISA) kit.

10. The breast cancer diagnostic kit according to claim 9, wherein the ELISA is one or more selected from the group consisting of direct ELISA, indirect ELISA, direct sandwich ELISA and indirect sandwich ELISA.

11. A method of providing information necessary for breast cancer diagnosis, comprising:
(a) bringing the monoclonal antibody or an antigen-binding fragment thereof of claim 1 into contact with a biological sample isolated from a subject suspected of having breast cancer;
(b) measuring an expression level of the thioredoxin-1 protein binding to the monoclonal antibody or an antigen-binding fragment thereof in the biological sample through the formation of an antigen-antibody complex; and
(c) comparing the expression level of the thioredoxin-1 protein, measured in step (b) with that of a control and, if the protein expression level is higher than that of the control, determining the subject to be a breast cancer patient.

12. The method according to claim 11, wherein the expression level of the thioredoxin-1 protein is measured by any one method selected from the group consisting of western blotting, ELISA, sandwich ELISA, a radioimmunoassay, radioimmunoprecipitation, Ouchterlony immunodiffusion, an immunoprecipitation assay, a complement fixation assay, an immunochromatographic assay, FACS and a protein chip assay.

13. The method according to claim 11, wherein the isolated biological sample is any one or more selected from the group consisting of whole blood, serum, plasma, breast tissue and breast cells.

14. A method of providing information necessary for breast cancer diagnosis, comprising:
(a) coating a solid support with the monoclonal antibody or an antigen-binding fragment thereof of (ii) of claim 1;
(b) applying a biological sample isolated from a subject suspected of having breast cancer to the coated solid support;
(c) removing an unbound sample;
(d) applying the monoclonal antibody or an antigen-binding fragment thereof of (i) of claim 3 to the solid support;
(e) removing an unbound monoclonal antibody or an antigen-binding fragment thereof;
(f) measuring an expression level of the thioredoxin-1 protein; and
(g) comparing the expression level of the thioredoxin-1 protein, measured in step (f), with a control, and, if the protein expression level is higher than that of the control, determining the subject to be a breast cancer patient.

15. The method according to claim 14, wherein the expression level of the thioredoxin-1 protein is measured by any one method selected from the group consisting of western blotting, ELISA, sandwich ELISA, a radioimmunoassay, radioimmunoprecipitation, Ouchterlony immunodiffusion, an immunoprecipitation assay, a complement fixation assay, an immunochromatographic assay, FACS and a protein chip assay.

16. The method according to claim 14, wherein the isolated biological sample is any one or more selected from the group consisting of whole blood, serum, plasma, breast tissue and breast cells.

* * * * *

UNITED STATES PATENT AND TRADEMARK OFFICE
CERTIFICATE OF CORRECTION

| | | |
|---|---|---|
| PATENT NO. | : 11,002,739 B2 | Page 1 of 1 |
| APPLICATION NO. | : 16/332623 | |
| DATED | : May 11, 2021 | |
| INVENTOR(S) | : Kyong Hoon Suh et al. | |

It is certified that error appears in the above-identified patent and that said Letters Patent is hereby corrected as shown below:

In the Claims

Claim 14, Column 54, Line 45:
Delete "of claim 3" and replace with -- of claim 1 --.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 28

<210> SEQ ID NO 1
<211> LENGTH: 6
<212> TYPE: PRT

```
<213> ORGANISM: Artificial
<220> FEATURE:
<223> OTHER INFORMATION: Light chain CDR1 of monoclonal antibody B266-1

<400> SEQUENCE: 1

Ser Arg Ile Ser Tyr Met
1               5

<210> SEQ ID NO 2
<211> LENGTH: 3
<212> TYPE: PRT
<213> ORGANISM: Artificial
<220> FEATURE:
<223> OTHER INFORMATION: Light chain CDR2 of monoclonal antibody B266-1

<400> SEQUENCE: 2

Asp Thr Ser
1

<210> SEQ ID NO 3
<211> LENGTH: 7
<212> TYPE: PRT
<213> ORGANISM: Artificial
<220> FEATURE:
<223> OTHER INFORMATION: Light chain CDR3 of monoclonal antibody B266-1

<400> SEQUENCE: 3

His Gln Arg Ser Ser Tyr Pro
1               5

<210> SEQ ID NO 4
<211> LENGTH: 11
<212> TYPE: PRT
<213> ORGANISM: Artificial
<220> FEATURE:
<223> OTHER INFORMATION: Light chain CDR1 of monoclonal antibody B264

<400> SEQUENCE: 4

Gln Ser Ile Val His Ser Asn Gly Asn Thr Tyr
1               5                   10

<210> SEQ ID NO 5
<211> LENGTH: 3
<212> TYPE: PRT
<213> ORGANISM: Artificial
<220> FEATURE:
<223> OTHER INFORMATION: Light chain CDR2 of monoclonal antibody B264

<400> SEQUENCE: 5

Lys Val Ser
1

<210> SEQ ID NO 6
<211> LENGTH: 7
<212> TYPE: PRT
<213> ORGANISM: Artificial
<220> FEATURE:
<223> OTHER INFORMATION: Light chain CDR3 of monoclonal antibody B264

<400> SEQUENCE: 6

Phe Gln Gly Ser His Val Pro
1               5

<210> SEQ ID NO 7
<211> LENGTH: 8
<212> TYPE: PRT
<213> ORGANISM: Artificial
```

```
<220> FEATURE:
<223> OTHER INFORMATION: Heavy chain CDR1 of monoclonal antibody B266-1

<400> SEQUENCE: 7

Gly Phe Asn Ile Lys Asp Thr Phe
1               5

<210> SEQ ID NO 8
<211> LENGTH: 8
<212> TYPE: PRT
<213> ORGANISM: Artificial
<220> FEATURE:
<223> OTHER INFORMATION: Heavy chain CDR2 of monoclonal antibody B266-1

<400> SEQUENCE: 8

Ile Asp Pro Ala Asn Gly Asn Thr
1               5

<210> SEQ ID NO 9
<211> LENGTH: 1
<212> TYPE: PRT
<213> ORGANISM: Artificial
<220> FEATURE:
<223> OTHER INFORMATION: Heavy chain CDR3 of monoclonal antibody B266-1

<400> SEQUENCE: 9

Ala
1

<210> SEQ ID NO 10
<211> LENGTH: 94
<212> TYPE: PRT
<213> ORGANISM: Artificial
<220> FEATURE:
<223> OTHER INFORMATION: Light chain variable region of monoclonal
      antibody B266-1

<400> SEQUENCE: 10

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Ile Ser Tyr Met
            20                  25                  30

Tyr Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys His Gln Arg Ser Ser Tyr Pro
                85                  90

<210> SEQ ID NO 11
<211> LENGTH: 100
<212> TYPE: PRT
<213> ORGANISM: Artificial
<220> FEATURE:
<223> OTHER INFORMATION: Light chain variable region of monoclonal
      antibody B264

<400> SEQUENCE: 11

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30
```

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro
            100

<210> SEQ ID NO 12
<211> LENGTH: 97
<212> TYPE: PRT
<213> ORGANISM: Artificial
<220> FEATURE:
<223> OTHER INFORMATION: Heavy chain variable region of monoclonal
      antibody B266-1

<400> SEQUENCE: 12

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Phe Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
 50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala

<210> SEQ ID NO 13
<211> LENGTH: 212
<212> TYPE: PRT
<213> ORGANISM: Artificial
<220> FEATURE:
<223> OTHER INFORMATION: Light chain of monoclonal antibody B266

<400> SEQUENCE: 13

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Ile Ser Tyr Met
            20                  25                  30

Tyr Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
 50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys His Gln Arg Ser Ser Tyr Pro Thr Phe
                85                  90                  95

Gly Ala Gly Thr Lys Leu Glu Leu Lys Arg Ala Asp Ala Ala Pro Thr
            100                 105                 110

Val Ser Ile Phe Pro Pro Ser Ser Glu Gln Leu Thr Ser Gly Gly Ala

```
              115                 120                 125
Ser Val Val Cys Phe Leu Asn Asn Phe Tyr Pro Lys Asp Ile Asn Val
    130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
                195                 200                 205

Arg Asn Glu Cys
210
```

<210> SEQ ID NO 14
<211> LENGTH: 452
<212> TYPE: PRT
<213> ORGANISM: Artificial
<220> FEATURE:
<223> OTHER INFORMATION: Heavy chain of monoclonal antibody B266

<400> SEQUENCE: 14

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
                20                  25                  30

Phe Met His Trp Val Lys Gln Arg Pro Glu Gln Gly Leu Glu Trp Ile
            35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Leu Leu Gln Tyr Ser Ala Met Asp Tyr Trp Gly Gln Gly Thr Ser
            100                 105                 110

Val Thr Val Ser Ser Ala Lys Thr Thr Pro Pro Ser Val Tyr Pro Leu
        115                 120                 125

Ala Pro Gly Cys Gly Asp Thr Thr Gly Ser Ser Val Thr Leu Gly Cys
    130                 135                 140

Leu Val Lys Gly Tyr Phe Pro Glu Ser Val Thr Val Thr Trp Asn Ser
145                 150                 155                 160

Gly Ser Leu Ser Ser Ser Val His Thr Phe Pro Ala Leu Leu Gln Ser
                165                 170                 175

Gly Leu Tyr Thr Met Ser Ser Ser Val Thr Val Pro Ser Ser Thr Trp
            180                 185                 190

Pro Ser Gln Thr Val Thr Cys Ser Val Ala His Pro Ala Ser Ser Thr
        195                 200                 205

Thr Val Asp Lys Lys Leu Glu Pro Ser Gly Pro Ile Ser Thr Ile Asn
    210                 215                 220

Pro Cys Pro Pro Cys Lys Glu Cys His Lys Cys Pro Ala Pro Asn Leu
225                 230                 235                 240

Glu Gly Gly Pro Ser Val Phe Ile Phe Pro Pro Asn Ile Lys Asp Val
                245                 250                 255

Leu Met Ile Ser Leu Thr Pro Lys Val Thr Cys Val Val Val Asp Val
```

```
                    260                 265                 270
    Ser Glu Asp Asp Pro Asp Val Gln Ile Ser Trp Phe Val Asn Asn Val
                275                 280                 285

Glu Val His Thr Ala Gln Thr Gln Thr His Arg Glu Asp Tyr Asn Ser
                290                 295                 300

Thr Ile Arg Val Val Ser Thr Leu Pro Ile Gln His Gln Asp Trp Met
    305                 310                 315                 320

Ser Gly Lys Glu Phe Lys Cys Lys Val Asn Asn Lys Asp Leu Pro Ser
                    325                 330                 335

Pro Ile Glu Arg Thr Ile Ser Lys Ile Lys Gly Leu Val Arg Ala Pro
                340                 345                 350

Gln Val Tyr Ile Leu Pro Pro Ala Glu Gln Leu Ser Arg Lys Asp
                355                 360                 365

Val Ser Leu Thr Cys Leu Val Val Gly Phe Asn Pro Gly Asp Ile Ser
                370                 375                 380

Val Glu Trp Thr Ser Asn Gly His Thr Glu Glu Asn Tyr Lys Asp Thr
    385                 390                 395                 400

Ala Pro Val Leu Asp Ser Asp Gly Ser Tyr Phe Ile Tyr Ser Lys Leu
                    405                 410                 415

Asn Met Lys Thr Ser Lys Trp Glu Lys Thr Asp Ser Phe Ser Cys Asn
                420                 425                 430

Val Arg His Glu Gly Leu Lys Asn Tyr Tyr Leu Lys Lys Thr Ile Ser
                435                 440                 445

Arg Ser Pro Gly
        450

<210> SEQ ID NO 15
<211> LENGTH: 219
<212> TYPE: PRT
<213> ORGANISM: Artificial
<220> FEATURE:
<223> OTHER INFORMATION: Light chain of monoclonal antibody B264

<400> SEQUENCE: 15

Asp Val Leu Met Thr Gln Thr Pro Leu Ser Leu Pro Val Ser Leu Gly
    1               5                   10                  15

Asp Gln Ala Ser Ile Ser Cys Arg Ser Gln Ser Ile Val His Ser
                20                  25                  30

Asn Gly Asn Thr Tyr Leu Glu Trp Tyr Leu Gln Lys Pro Gly Gln Ser
                35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
    65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                    100                 105                 110

Arg Ala Asp Ala Ala Pro Thr Val Ser Ile Phe Pro Pro Ser Ser Glu
                115                 120                 125

Gln Leu Thr Ser Gly Gly Ala Ser Val Val Cys Phe Leu Asn Asn Phe
                130                 135                 140

Tyr Pro Lys Asp Ile Asn Val Lys Trp Lys Ile Asp Gly Ser Glu Arg
    145                 150                 155                 160

Gln Asn Gly Val Leu Asn Ser Trp Thr Asp Gln Asp Ser Lys Asp Ser
```

```
                    165                 170                 175
Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
            195                 200                 205

Pro Ile Val Lys Ser Phe Asn Arg Asn Glu Cys
            210                 215

<210> SEQ ID NO 16
<211> LENGTH: 443
<212> TYPE: PRT
<213> ORGANISM: Artificial
<220> FEATURE:
<223> OTHER INFORMATION: heavy chain of monoclonal antibody B264

<400> SEQUENCE: 16

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Thr Ser Asp Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Glu Gly Gly Phe Leu Tyr Tyr Phe Asp Tyr Trp Gly Gln Gly
            100                 105                 110

Thr Thr Leu Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
```

|  |  |  |  |  | 305 |  |  |  |  | 310 |  |  |  |  | 315 |  |  |  |  | 320 |
|---|---|---|---|---|---|---|---|---|---|---|---|---|---|---|---|---|---|---|---|---|

Ser Ala Ala Phe Pro Ala Pro Ile Glu Lys Thr Ile Ser Lys Thr Lys
                    325                 330                 335

Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
                355                 360                 365

Phe Pro Glu Asp Ile Thr Val Glu Trp Gln Trp Asn Gly Gln Pro Ala
            370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                    405                 410                 415

Asn Thr Phe Thr Cys Ser Val Leu His Glu Gly Leu His Asn His His
                420                 425                 430

Thr Glu Lys Ser Leu Ser His Ser Pro Gly Lys
                435                 440

<210> SEQ ID NO 17
<211> LENGTH: 660
<212> TYPE: DNA
<213> ORGANISM: Artificial
<220> FEATURE:
<223> OTHER INFORMATION: Light chain of monoclonal antibody B264

<400> SEQUENCE: 17

```
gacgtgctga tgacacagac accactcagc ctccctgtga gcctgggcga ccaggcctct      60
atttcttgcc ggtctagcca gagcatcgtg cactccaacg caacacata cttggagtgg     120
tatctacaga agcccggcca gtcccctaag ctgctgatat acaaggtgtc taaccgcttc     180
tccggcgtgc ccgacaggtt ctctggcagc ggctctggca ccgacttcac cctcaaaata     240
tctagggtgg aggccgagga cctgggcgtg tactactgct ccagggctc ccacgttcca     300
tacacattcg gcggcggcac aaagttggaa attaagcgcg ctgacgcagc cccaacagtg     360
agcatctttc ctccatcctc tgaacaactt acctctggag gagcctctgt ggtgtgtttc     420
ctgaacaact tctacccaaa ggacatcaat gtgaagtgga agattgatgg ctctgagaga     480
cagaatggag tgctgaactc ctggacagac aggacagca aggacagcac ctacagtatg     540
agtagcaccc tgaccctgac aaggatgaa tatgagagac acaactccta cacttgtgag     600
gctacccaca agaccagcac cagcccaatt gtcaaatcct tcaacaggaa tgagtgttaa     660
```

<210> SEQ ID NO 18
<211> LENGTH: 1332
<212> TYPE: DNA
<213> ORGANISM: Artificial
<220> FEATURE:
<223> OTHER INFORMATION: Heavy chain of monoclonal antibody B264

<400> SEQUENCE: 18

```
caggtgcagc tccagcagtc cggcgccgaa ctggccagac tggcgccag cgtgaagatg      60
agctgcaagg cctccggcta cacattcaca tcttacacca tgcactgggt gaagcagaga     120
cccggccagg gcctggagtg gattggctac attaacccaa catccgacta cacaaactac     180
aaccagaagt tcaaggacaa ggccacactc accgccgaca gtcttctag cacagcctac     240
atgcagctgt ctagcctgac aagcgaggac tctgccgtgt acttctgcgc ctctgagggc     300
ggcttcctgt actacttcga ctactggggc cagggcacca ccctgaccgt gtcctctgcc     360
```

```
aaaacgacac cccatctgt ctatccactg gcccctggat ctgctgccca aactaactcc    420
atggtgaccc tgggatgcct ggtcaagggc tatttccctg agccagtgac agtgacctgg    480
aactctggat ccctgtccag cggtgtgcac accttccag ctgtcctgca gtctgacctc    540
tacactctga gcagctcagt gactgtcccc tccagcacct ggcccagcga gaccgtcacc    600
tgcaacgttg cccacccggc cagcagcacc aaggtggaca gaaaattgt gcccagggat    660 tgtggttgta agccttgcat atgtacagtc ccagaagtat catctgtctt catcttcccc    720
ccaaagccca aggatgtgct caccattact ctgactccta aggtcacgtg tgttgtggta    780
gacatcagca aggatgatcc cgaggtccag ttcagctggt ttgtagatga tgtggaggtg    840
cacacagctc agacgcaacc ccgggaggag cagttcaaca gcactttccg ctcagtcagt    900
gaacttccca tcatgcacca ggactggctc aatggcaagg agttcaaatg cagggtcaac    960
agtgcagctt tccctgcccc catcgagaaa accatctcca aaaccaaagg cagaccgaag   1020
gctccacagg tgtacaccat tccacctccc aaggagcaga tggccaagga taaagtcagt   1080
ctgacctgca tgataacaga cttcttccct gaagacatta ctgtggagtg cagtggaat   1140 gggcagccag cggagaacta caagaacact cagcccatca tggacacaga tggctcttac   1200
ttcgtctaca gcaagctcaa tgtgcagaag agcaactggg aggcaggaaa tactttcacc   1260
tgctctgtgt acatgagggg cctgcacaac accatactg agaagagcct ctcccactct   1320
cctggtaaat aa                                                       1332

<210> SEQ ID NO 19
<211> LENGTH: 639
<212> TYPE: DNA
<213> ORGANISM: Artificial
<220> FEATURE:
<223> OTHER INFORMATION: Light chain of monoclonal antibody B266

<400> SEQUENCE: 19
cagatcgtgc tcacacagtc tccagccatc atgagcgcct ctcctggcga aaggtgaca     60 atgacctgct ctgcctctag ccgcatttct tacatgtact ggtatcagca gaagccaggc    120
acctccccta agaggtggat atacgacaca tccaagctgg cctccggcgt gcccgcccgg    180
ttcagcggct ctggcagcgg cacaagctac tccctgacaa ttagcacgat ggaggccgag    240
gacgccgcca catactactg ccaccagcgc tcgtcctacc caacattcgg cgccggcaca    300
aaattggaac tgaagagagc tgacgcagcc ccaacagtga gcatctttcc tccatcctct    360
gaacaactta cctctggagg agcctctgtg gtgtgtttcc tgaacaactt ctacccaaag    420
gacatcaatg tgaagtggaa gattgatggc tctgagagac agaatggagt gctgaactcc    480
tggacagacc aggacagcaa ggacagcacc tacagtatga gtagcaccct gaccctgacc    540
aaggatgaat atgagagaca caactcctac acttgtgagg ctacccacaa gaccagcacc    600
agcccaattg tcaaatcctt caacaggaat gagtgttaa                           639

<210> SEQ ID NO 20
<211> LENGTH: 1359
<212> TYPE: DNA
<213> ORGANISM: Artificial
<220> FEATURE:
<223> OTHER INFORMATION: heavy chain of monoclonal antibody B266

<400> SEQUENCE: 20
gaggtgcagt tacaacagtc cggcgccgag ctagtgaagc caggcgccag cgtgaagctg     60
```

-continued

```
tcttgcacag ccagcggctt caacattaag gacaccttca tgcactgggt gaagcagaga    120
cctgagcagg gcttagagtg gattggccgg atcgaccccg ccaacggcaa cacaaagtac    180
gacccaaagt tccagggcaa ggccacaatt accgccgaca catcttccaa cacagcctac    240
ctccagctgt cgtctctcac cagcgaggac accgccgtgt actactgcgc cctgctccag    300
tactccgcga tggactactg gggccagggc acatctgtga ccgtgtctag cgccaagacc    360
accccaccat ccgtgtaccc actcgcccca ggctgcggcg acaccacagg ctctagcgtg    420
acactgggct gcctggtgaa gggctacttc cccgagtctg tgacagtgac ctggaactct    480
ggctctctgt ctagctctgt gcacaccttc cccgccctgc tgcaatccgg cctgtacaca    540
atgtcttctt ctgtgacagt gcctagctct acatggccat ctcagacagt gacatgctct    600
gtggcccacc ccgcctctag cacaaccgtg gacaagaagc tggagccatc cggccctatt    660
tctacaatta acccttgccc tccttgcaaa gaatgccaca agtgccccgc cccaaacctg    720
gagggcggcc cttctgtgtt cattttccct cctaacatta aggacgtgct gatgatcagc    780
ctcaccccaa aggtgacatg cgtggtggtg gacgtgtccg aggacgaccc tgacgtgcag    840
atttcttggt tcgtgaacaa cgtggaggtg cacaccgccc agacccagac ccaccgggag    900
gactacaact ccaccattcg ggtggtgtct acactgccta ttcagcacca ggactggatg    960
agcggcaaag agttcaagtg caaggtgaac aacaaggacc tgccatctcc tattgagaga   1020
acaatttcta agattaaggg cctggtgcgc gcccctcagg tgtacattct gcctcctccc   1080
gccgagcagc tgagccggaa ggacgtgtcc ctcacatgcc tcgtggtggg cttcaaccct   1140
ggcgacatta gcgtggagtg gacatctaac ggccacacag aagaaaacta caaggacaca   1200
gcccctgtgc tcgactccga cggctcttac ttcatatact ctaagctgaa catgaaaaca   1260
tctaagtggg aaaagaccga ctctttctct tgcaacgtgc ggcacgaggg cctgaagaac   1320
tactacctca agaaaaccat tagcagaagt ccaggctaa                          1359
```

```

<210> SEQ ID NO 21
<211> LENGTH: 315
<212> TYPE: DNA
<213> ORGANISM: Artificial
<220> FEATURE:
<223> OTHER INFORMATION: Human Thioredoxin-1

<400> SEQUENCE: 21
atggtcaaac agatcgaatc aaaaaccgca tttcaagaag ccctggacgc cgctggtgac     60
aaactggtcg tggtggactt tagtgctacc tggtgcggcc cgtgtaaaat gattaaaccg    120
tttttccata gcctgtctga aaaatacagt aacgttatct ttctggaagt ggatgttgat    180
gactgccagg acgtcgcgag cgaatgcgaa gtgaaatgta tgccgacgtt ccagtttttc    240
aaaaaaggtc aaaaagtcgg tgaatttagc ggtgccaaca aagaaaaact ggaagccacg    300
attaacgaac tggtg                                                     315

<210> SEQ ID NO 22
<211> LENGTH: 22
<212> TYPE: DNA
<213> ORGANISM: Artificial
<220> FEATURE:
<223> OTHER INFORMATION: Human Thioredoxin-1 forward primer

<400> SEQUENCE: 22
taatggtcaa acagatcgaa tc                                              22
```

<210> SEQ ID NO 23
<211> LENGTH: 31
<212> TYPE: DNA
<213> ORGANISM: Artificial
<220> FEATURE:
<223> OTHER INFORMATION: Human Thioredoxin-1 reverse primer

<400> SEQUENCE: 23
caccagttcg ttaatcgtgg taatgaaagc t                              31

<210> SEQ ID NO 24
<211> LENGTH: 344
<212> TYPE: DNA
<213> ORGANISM: Artificial
<220> FEATURE:
<223> OTHER INFORMATION: multi-cloning site

<400> SEQUENCE: 24
cctaggctat aatggtcaaa cagatcgaat caaaaaccgc atttcaagaa gccctggacg      60
ccgctggtga caaactggtc gtggtggact ttagtgctac ctggtgcggc ccgtgtaaaa     120
tgattaaacc gttttttccat agcctgtctg aaaaatacag taacgttatc tttctggaag    180
tggatgttga tgactgccag gacgtcgcga gcgaatgcga agtgaaatgt atgccgacgt     240
tccagttttt caaaaaggt caaaaagtcg gtgaatttag cggtgccaac aaagaaaaac      300
tggaagccac gattaacgaa ctggtgatta ctttcgatag atct                     344

<210> SEQ ID NO 25
<211> LENGTH: 212
<212> TYPE: PRT
<213> ORGANISM: Artificial
<220> FEATURE:
<223> OTHER INFORMATION: light chain of antibody 9G7

<400> SEQUENCE: 25

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Arg Leu Ser Tyr Met
            20                  25                  30

Tyr Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys His Gln Arg Ser Ser Tyr Pro Thr Phe
                85                  90                  95

Gly Ala Gly Thr Lys Leu Glu Ile Lys Arg Ala Asp Ala Ala Pro Thr
            100                 105                 110

Val Ser Ile Phe Pro Pro Ser Ser Glu Gln Leu Thr Ser Gly Gly Ala
        115                 120                 125

Ser Val Val Cys Phe Leu Asn Asn Phe Tyr Pro Lys Asp Ile Asn Val
    130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

-continued

Glu Ala Thr His Lys Thr Ser Thr Ser Pro Ile Val Lys Ser Phe Asn
            195                 200                 205

Arg Asn Glu Cys
    210

<210> SEQ ID NO 26
<211> LENGTH: 452
<212> TYPE: PRT
<213> ORGANISM: Artificial
<220> FEATURE:
<223> OTHER INFORMATION: heavy chain of antibody 9GF

<400> SEQUENCE: 26

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Phe Met His Trp Val Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Leu Leu Gln Tyr Ser Ala Met Asp Tyr Trp Gly Gln Gly Thr Ser
            100                 105                 110

Val Thr Val Ser Ser Ala Lys Thr Thr Pro Pro Ser Val Tyr Pro Leu
        115                 120                 125

Ala Pro Gly Cys Gly Asp Thr Thr Gly Ser Ser Val Thr Leu Gly Cys
    130                 135                 140

Leu Val Lys Gly Tyr Phe Pro Glu Ser Val Thr Val Thr Trp Asn Ser
145                 150                 155                 160

Gly Ser Leu Ser Ser Ser Val His Thr Phe Pro Ala Leu Leu Gln Ser
                165                 170                 175

Gly Leu Tyr Thr Met Ser Ser Ser Val Thr Val Pro Ser Ser Thr Trp
            180                 185                 190

Pro Ser Gln Thr Val Thr Cys Ser Val Ala His Pro Ala Ser Ser Thr
        195                 200                 205

Thr Val Asp Lys Lys Leu Glu Pro Ser Gly Pro Ile Ser Thr Ile Asn
    210                 215                 220

Pro Cys Pro Pro Cys Lys Glu Cys His Lys Cys Pro Ala Pro Asn Leu
225                 230                 235                 240

Glu Gly Gly Pro Ser Val Phe Ile Phe Pro Pro Asn Ile Lys Asp Val
                245                 250                 255

Leu Met Ile Ser Leu Thr Pro Lys Val Thr Cys Val Val Val Asp Val
            260                 265                 270

Ser Glu Asp Asp Pro Asp Val Gln Ile Ser Trp Phe Val Asn Asn Val
        275                 280                 285

Glu Val His Thr Ala Gln Thr Gln Thr His Arg Glu Asp Tyr Asn Ser
    290                 295                 300

Thr Ile Arg Val Val Ser Thr Leu Pro Ile Gln His Gln Asp Trp Met
305                 310                 315                 320

Ser Gly Lys Glu Phe Lys Cys Lys Val Asn Asn Lys Asp Leu Pro Ser
                325                 330                 335

```
Pro Ile Glu Arg Thr Ile Ser Lys Ile Lys Gly Leu Val Arg Ala Pro
                340                 345                 350

Gln Val Tyr Ile Leu Pro Pro Ala Glu Gln Leu Ser Arg Lys Asp
            355                 360                 365

Val Ser Leu Thr Cys Leu Val Val Gly Phe Asn Pro Gly Asp Ile Ser
        370                 375                 380

Val Glu Trp Thr Ser Asn Gly His Thr Glu Glu Asn Tyr Lys Asp Thr
385                 390                 395                 400

Ala Pro Val Leu Asp Ser Asp Gly Ser Tyr Phe Ile Tyr Ser Lys Leu
                405                 410                 415

Asn Met Lys Thr Ser Lys Trp Glu Lys Thr Asp Ser Phe Ser Cys Asn
            420                 425                 430

Val Arg His Glu Gly Leu Lys Asn Tyr Tyr Leu Lys Lys Thr Ile Ser
        435                 440                 445

Arg Ser Pro Gly
    450
```

```
<210> SEQ ID NO 27
<211> LENGTH: 219
<212> TYPE: PRT
<213> ORGANISM: Artificial
<220> FEATURE:
<223> OTHER INFORMATION: light chain of antibody 2B4

<400> SEQUENCE: 27

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Leu Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 28
<211> LENGTH: 442
```

```
<212> TYPE: PRT
<213> ORGANISM: Artificial
<220> FEATURE:
<223> OTHER INFORMATION: heavy chain of antibody 2B4

<400> SEQUENCE: 28

Gln Val Gln Leu Gln Gln Ser Phe Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Thr Ser Asp Tyr Thr Asn Tyr Asn Gln Lys Phe
50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Ser Glu Gly Gly Phe Leu Tyr Tyr Phe Asp Tyr Trp Gly Gln Gly
            100                 105                 110

Thr Thr Leu Thr Val Ser Ser Ala Lys Thr Thr Pro Pro Ser Val Tyr
        115                 120                 125

Pro Leu Ala Pro Gly Ser Ala Ala Gln Thr Asn Ser Asn Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
370                 375                 380
```

-continued

```
Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
                420                 425                 430

Thr Glu Lys Ser Leu Ser His Ser Pro Gly
            435                 440
```